(12) United States Patent
Zheng et al.

(10) Patent No.: US 10,556,985 B2
(45) Date of Patent: *Feb. 11, 2020

(54) NITROGEN-CONTAINING HETEROCYCLIC EPOXY CURING AGENTS, COMPOSITIONS AND METHODS

(71) Applicant: Evonik Operations GmbH, Essen (DE)

(72) Inventors: Shiying Zheng, Center Valley, PA (US); Sudhir Ananthachar, Hillsborough, NJ (US); Shafiq Nisarali Fazel, Allentown, PA (US); Michael Ian Cook, DeMeern (NL); Robert Marjo Theodoor Rasing, Didam (NL); Wei Cao, Orefield, PA (US); Edze Jan Tijsma, Zeist (NL)

(73) Assignee: Evonik Operations GmbH, Essen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/343,632

(22) Filed: Nov. 4, 2016

(65) Prior Publication Data

US 2017/0137562 A1    May 18, 2017

Related U.S. Application Data

(60) Provisional application No. 62/256,262, filed on Nov. 17, 2015.

(51) Int. Cl.
| | |
|---|---|
| C08G 59/50 | (2006.01) |
| C07D 233/02 | (2006.01) |
| C08G 59/56 | (2006.01) |
| C08G 59/60 | (2006.01) |
| C09D 163/00 | (2006.01) |

(52) U.S. Cl.
CPC ....... C08G 59/5073 (2013.01); C07D 233/02 (2013.01); C08G 59/56 (2013.01); C08G 59/60 (2013.01); C09D 163/00 (2013.01)

(58) Field of Classification Search
None
See application file for complete search history.

(56) References Cited

U.S. PATENT DOCUMENTS

| | | | |
|---|---|---|---|
| 2,643,977 | A | 6/1953 | Hughes |
| 4,269,742 | A | 5/1981 | Goeke et al. |
| 4,289,869 | A | 9/1981 | Zengel et al. |
| 4,533,682 | A | 8/1985 | Tortorello et al. |
| 4,877,578 | A | 10/1989 | Zetlmeisl et al. |
| 6,465,601 | B1 | 10/2002 | Wiesendanger et al. |
| 8,147,964 | B2 | 4/2012 | Vedage et al. |
| 8,168,296 | B2 | 5/2012 | Vedage et al. |
| 8,518,547 | B2 | 8/2013 | Vedage et al. |
| 2009/0029175 | A1* | 1/2009 | Vedage .............. C08G 59/502 428/418 |

FOREIGN PATENT DOCUMENTS

| | | |
|---|---|---|
| CN | 103333136 | 10/2013 |
| DE | 32321509 | 11/1973 |
| EP | 0458502 A2 | 11/1991 |
| JP | 5408612 | 2/2014 |
| WO | 2013003202 | 1/2013 |

OTHER PUBLICATIONS

Huntsman Ethyleneamines: A Global Profile of Products and Services; Jan. 1, 2007 (76 pages).
Takeo Araki, et al.; Site-Selective Derivatization of Oligoethylenimines Using Five-Membered-Ring Protection Method; Macromolecules; vol. 21; No. 7; Jan. 1, 1988; Retrieved from the Internet: http://pubs.acs.org/doi/pdf/10.1021/ma00185a018 on Feb. 2, 2016 (7 pages).
J. Van Alphen; N.N'-Di-(Benzyl)-Ethylenediamine (Alkylated ethylenediamine derivatives I); Recueil des; vol. 54, No. 2, pp. 93-96, Sep. 3, 1935; Amsterdam, NL; XP055346671 (4 pages).
Jack Hine and Kenneth W. Narducy; Imines, Imidazolidines, and Imidazolidinium Ions from the Reactions of Ethylenediamine Derivates with Isobutyraldehyde and Acetone; May 1, 1973; Retrieved from the Internet: http://pubs.acs.org/doi/pdf/10.1021/ja00791a047 on Feb. 16, 2017 (7 pages).
European Search Report dated Mar. 8, 2017 corresponding to European Application No. 16199165.8 filed Nov. 16, 2016. (11 pages).

(Continued)

*Primary Examiner* — Robert T Butcher
(74) *Attorney, Agent, or Firm* — Andrew H. Chung; Linda S. Li; Jason S. Ngui

(57) ABSTRACT

Amine-epoxy curing agents are disclosed including at least one saturated heterocyclic compound having two nitrogen heteroatoms according to formula (I) and at least one saturated fused bicyclic heterocyclic compound having three nitrogen heteroatoms according to formula (II):

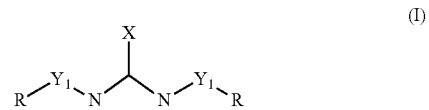

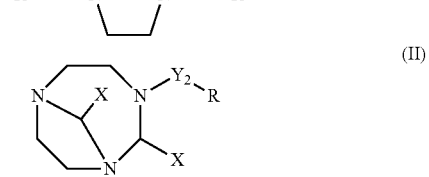

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms or a divalent polyethylene polyamine derivative having 1 to 8 nitrogen atoms, $Y_2$ is a direct bond or a divalent polyethylene polyamine group having 1 to 7 nitrogen atoms and R is independently a hydrogen atom or a group selected from $C_1$-$C_8$ linear, cyclic, and branched alkyl, alkenyl, and alkaryl groups.

8 Claims, 2 Drawing Sheets

(56) References Cited

OTHER PUBLICATIONS

H. Lee and K. Neville "Handbook of Epoxy Resins" McGraw Hill, New York, 1967, pp. 5-1 to 5-25.
Araki et al, "Site-Selective Derivatization of Oligoethylenimines Using Five-Membered-Ring Protection Method", Macromolecules, vol. 21, No. 7, pp. 1995-2001 (1988).
Khune and Ghatge, "Amine Aldehyde Condensation Products for Stabilization of Natural Rubber Latex Foam", Journal of Macrornolecular Science: Part A—Chemistry: Pure and Applied Chemistry, col. A(15), No. 1, pp. 153-168 (1981).
Tanaka et al, "Synthesis and Characteristics of Epoxides", in C. A. May, ed., Epoxy Resins Chemistry and Technology (Marcel Dekker, 1988).
Ukrainskii Khimicheskii Zhurnal (Russian Edition), vol. 54, Issue: 4, pp. 387-9, Journal, 1988.

\* cited by examiner

Primary Amine Conversion Determined By Near Infrared Spectroscopy

NITROGEN-CONTAINING HETEROCYCLIC EPOXY CURING AGENTS, COMPOSITIONS AND METHODS

CROSS-REFERENCE TO RELATED APPLICATIONS

This application claims priority from U.S. Ser. No. 62/256,262 filed Nov. 17, 2015 having the same title, which is incorporated herein by reference in its entirety.

BACKGROUND OF THE INVENTION

The present invention is directed to nitrogen-containing heterocyclic epoxy curing agents, compositions, and methods.

Epoxies are known for their excellent adhesion, chemical and heat resistance. In addition they also have good-to-excellent mechanical properties, and good electrical insulating properties. Cured epoxy resin systems are found in an extensive range of applications within the coatings, adhesives, and composites markets. Specific examples include epoxy composite using carbon fiber and fiberglass reinforcements, structural adhesives, protective coatings for metal surface, and construction products for concrete, cementitious or ceramic substrates, often referred to as civil engineering applications such as formulations for concrete flooring.

Cured epoxy resin systems consist of two components that can chemically react with each other to form a cured epoxy, which is a hard, duroplastic material. The first component is an epoxy resin and the second component is a curing agent, often referred to a hardener. Epoxy resins are substances or mixtures which contain epoxide groups. The curing agents include compounds which are reactive to the epoxide groups of the epoxy resins, such as amines, carboxylic acid, and mercaptanes (H. Lee and K. Neville "Handbook of Epoxy Resins" McGraw Hill, New York, 1967, pages 5-1 to 5-24). The epoxy resins can be cross-linked or cured by curing agents. The curing process is the chemical reaction of the epoxide groups in the epoxy resins and the reactive groups in the curing agents. The curing converts the epoxy resins, which have a relatively low molecular weight, into relatively high molecular weight materials by chemical addition of the curing agents to the epoxy resins. Additionally, the curing agent can contribute to many of the properties of the cured epoxy.

As noted above, epoxy resins are crosslinked or cured in order to develop certain characteristics. Many of these industrial applications mentioned require technology which can provide a faster return to service under application conditions specific to the industries in which they are used. For coatings and civil engineering, this is mainly the market need for improved reactivity and performance at low application temperatures, typical <10° C. and more often below 0° C., whereas in structural adhesives and composites the requirement can be for high reactivity of the curing agent at elevated temperature in the range 50° C. to 150° C.

However, many epoxy coatings suffer from slow cure at low application temperatures (≤5° C.) and a common side effect of the slow cure is that coatings can develop poor surface defects and a greasy surface appearance referred to as blushing, carbamation of or water spotting. These problems are in part attributed to the slow amine-epoxy reaction rate and partial incompatibility between the amine curing agent and epoxy resin. The incompatibility causes phase separation and amine migration to the coating surface. This results in incomplete amine-epoxy reaction and insufficient crosslinking which can lead to poor physical properties and poor coating performance. If free amine is present on the surface for too long a period, then the amine will react with water and carbon dioxide in the atmosphere and develop a white film on the surface which can lead to poor coating performance. Another problem is that the cure requires longer time for coating to set and dry, which means longer time to return to service or for the subsequent layer to be over coated. Traditionally the industry has used accelerators such as tertiary amines, and phenols and phenolic derivatives such as Mannich base compounds, salicylic acids to speed up amine-epoxy reaction at low temperature. However, incorporation of these species can only be used at low levels since they can cause the epoxy resin to homopolymerize and the resultant system to become brittle. Also they have a significant impact in causing the final epoxy system in be more prone to yellowing.

As also mentioned in the application area of structural adhesives and composites the need to reduce cycle times and increase productivity also requires a high reactivity of the curing agent with the epoxy resin. However, many of the curing agents used today providing high reactivity have drawbacks, which are either technical, such as uncontrolled reactivity, where a severe exotherm can result in damaging component parts during production as well as leading strong yellowing, in addition there are also health and safety concerns, where many materials may exhibit high vapor pressure and/or toxic labeling. Increasing regulatory pressure for both environmental and worker safety creates a need in these markets for curing agents with lower hazard ratings.

U.S. Pat. No. 4,269,742 discloses the preparation and use of Mannich base compounds as epoxy hardener to produce tack-free films at low temperature.

U.S. Pat. No. 6,465,601 discloses Mannich base compounds as accelerators for curable epoxy systems. There is a need in the industry to develop amine-epoxy compositions that are fast cure at low temperature and yellowing resistant.

WO 2013003202 discloses fast curing epoxy resin systems using mixtures of amine hardeners which are based on diethylene triamine (DETA). The epoxy resin systems and hardeners of this application are in particular suited for processes were short cycle times are desirable, such as resin transfer moulding under (high) pressure to make automotive parts. A significant issue with this application is the presence of DETA, which is coming under regulatory pressure because of health and safety aspects. There is a strong desire to replace DETA with an alternative curing agent, while retaining the benefits of good reactivity, such as low initial viscosity, good open time and fast cure. A high glass transition temperature would be a further advantage, if it could be obtained without comprising the needed curing characteristics.

U.S. Pat. No. 2,643,977 discloses a method of inhibiting metal corrosion using reaction product from diethylenetriamine with an aldehyde to form an imidazolidine intermediate and the final product was found to have corrosion-preventing properties.

U.S. Pat. No. 4,877,578 discloses the use of polyamine/formaldehyde reaction products as corrosion inhibitors for refinery overhead systems. The reaction products are described as a complex mixture including alkylene-bridged diethyleneamine triamines.

Chinese Patent Publication CN103333136 discloses a preparation method of a polyaminoamide cationic asphalt emulsifier. The patent discloses a reaction of polyethylene polyamine and formaldehyde, but does not describe the products of the reaction, and only discusses the products of the reaction as an intermediate product which is reacted with an organic acid and a quaternary ammonium reagent to generate a polyaminoamide cationic asphalt emulsifier.

German Patent Publication DE2321509 discloses a method for clarifying colored aqueous waste liquids or waste water, which includes use of water soluble condensation products of an aliphatic amino compound, such as diethylenetriamine, with a $C_1$ to $C_4$ aliphatic aldehyde.

Araki et al. in "Site-Selective Derivatization of Oligoethylenimines Using Five-Membered-Ring Protection Method", *Macromolecules*, vol. 21, no. 7, pp. 1996-2001 (1988), disclose a protocol for ring-closing oligoethylenimines to protect selected sites during organic synthesis and derivatization.

Khune and Ghatge in "Amine Aldehyde Condensation Products for Stabilization of Natural Rubber Latex Foam", *Journal of Macromolecular Science: Part A—Chemistry: Pure and Applied Chemistry*, col. A(15), no. 1, pp. 153-168 (1981) disclose ring-closing condensation reactions of formaldehyde with various aliphatic amines, but only monoamines or diamines are discussed as starting materials, and not triamines or larger species. These compounds are discussed with respect to their use as stabilizers for natural rubber latex foam.

The disclosure of the foregoing publications including patents and patent applications is hereby incorporated by reference.

BRIEF SUMMARY OF THE INVENTION

The present invention comprises an amine-epoxy curing agent. The amine-epoxy curing agent comprises at least one saturated heterocyclic compound having two nitrogen heteroatoms according to formula (I):

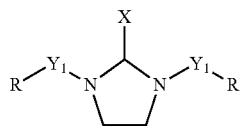
(I)

wherein X is selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups.

In another exemplary embodiment, the present invention comprises amine-epoxy curing agent composition comprising the contact product of:
(i) an amine-epoxy curing agent having at least one saturated heterocyclic compound having two nitrogen heteroatoms according to formula (I), and
(ii) at least one multifunctional amine having three or more active amine hydrogens per molecule.

In another exemplary embodiment, the present invention comprises an amine-epoxy composition. The amine-epoxy composition comprises an amine epoxy curing agent and at least one multifunctional epoxy resin. The amine-epoxy curing agent comprises at least one saturated heterocyclic compound having two nitrogen heteroatoms according to formula (I):

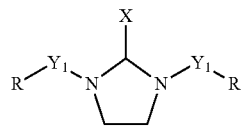
(I)

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups.

In another exemplary embodiment, the present invention comprises a method for forming a cured epoxy. The method for forming the cured epoxy comprises reacting an amine-epoxy curing agent with at least one multifunctional epoxy resin. The amine-epoxy curing agent comprises at least one saturated heterocyclic compound having two nitrogen heteroatoms according to formula (I):

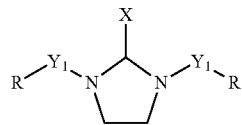
(I)

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups.

In another exemplary embodiment, the present invention comprises the amine-epoxy curing agent comprising at least one saturated heterocyclic compound having two nitrogen heteroatoms according to formula (I) and at least one saturated fused bicyclic heterocyclic compound having three nitrogen heteroatoms according to formula (II)

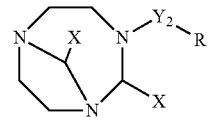
(II)

wherein X is independently selected from a hydrogen atom, a linear or branched $C_1$ to $C_4$ alkyl group and a substituted or un-substituted phenyl group, R is independently a hydrogen atom or a group selected from $C_1$-$C_8$ linear, cyclic, and branched alkyl, alkenyl, and alkaryl groups and $Y_2$ is a direct bond or a divalent polyethylene polyamine group having 1 to 7 nitrogen atoms.

In another exemplary embodiment, the amine-epoxy curing agent comprises a reaction product of a $C_1$ to $C_8$ aldehyde and a polyethylene polyamine having 3 to 10 nitrogen atoms, and the reaction product includes at least one saturated heterocyclic compound having two nitrogen heteroatoms according to formula (I).

In another exemplary embodiment, the amine-epoxy curing agent comprises a reaction product of a $C_1$ to $C_8$ aldehyde and a polyethylene polyamine having 3 to 10 nitrogen atoms, and the reaction product comprises at least one saturated heterocyclic compound having two nitrogen heteroatoms according to formula (I) and at least one saturated fused bicyclic heterocyclic compound having three nitrogen heteroatoms according to formula (II).

In another exemplary embodiment, the present invention comprises a process for preparing the amine-epoxy curing agent having at least one saturated heterocyclic compound having two nitrogen heteroatoms according to formula (I) by reacting a polyethylene polyamine having 3 to 10 nitrogen atoms with a $C_1$-$C_8$ aldehyde.

In another exemplary embodiment, the present invention comprises a process for preparing the amine-epoxy curing agent comprising at least one saturated heterocyclic compound having two nitrogen heteroatoms according to formula (I) and at least one saturated fused bicyclic heterocyclic compound having three nitrogen heteroatoms according to formula (II) by reacting a polyethylene polyamine having 3 to 10 nitrogen atoms with a $C_1$-$C_8$ aldehyde.

In one aspect of the present invention, the $C_1$ to $C_8$ aldehyde is formaldehyde or paraformaldehyde and the polyethylene polyamine compounds having 3 to 10 nitrogen atoms is diethylenetriamine. The reaction of formaldehyde and diethylenetriamine proceeds to generate reaction product containing formula (I) wherein X and R are H.

In another aspect of this invention, the amine-epoxy curing agent comprises solvent or plasticizer. A particularly suitable plasticizer is benzyl alcohol. The amine-epoxy curing agent may include up to about 20 wt %, alternatively up to about 30 wt %, alternatively up to about 40 wt %, alternatively up to about 50 wt % solvent or plasticizer, especially benzyl alcohol.

The amine-epoxy curing agent comprising at least one saturated heterocyclic compound having two nitrogen heteroatoms according to formula (I) has better compatibility with epoxy resin, particularly with most common epoxy resins based on bisphenol A or bisphenol F as well as polyepoxy novolac resins. The better compatibility reduces the separation of curing agent from epoxy especially at low temperature. Therefore curing agent and epoxy can react thoroughly and generate fully cured epoxy. Furthermore, the amine epoxy curing agent having at least one saturated heterocyclic compound having two nitrogen heteroatoms according to formula (I) also provides faster amine-epoxy reaction rate thus shorter time for film/coatings to dry. Still further epoxy cured with the amine-epoxy curing agent having at least one saturated heterocyclic compound having two nitrogen heteroatoms according to formula (I) exhibits good yellowing resistance.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
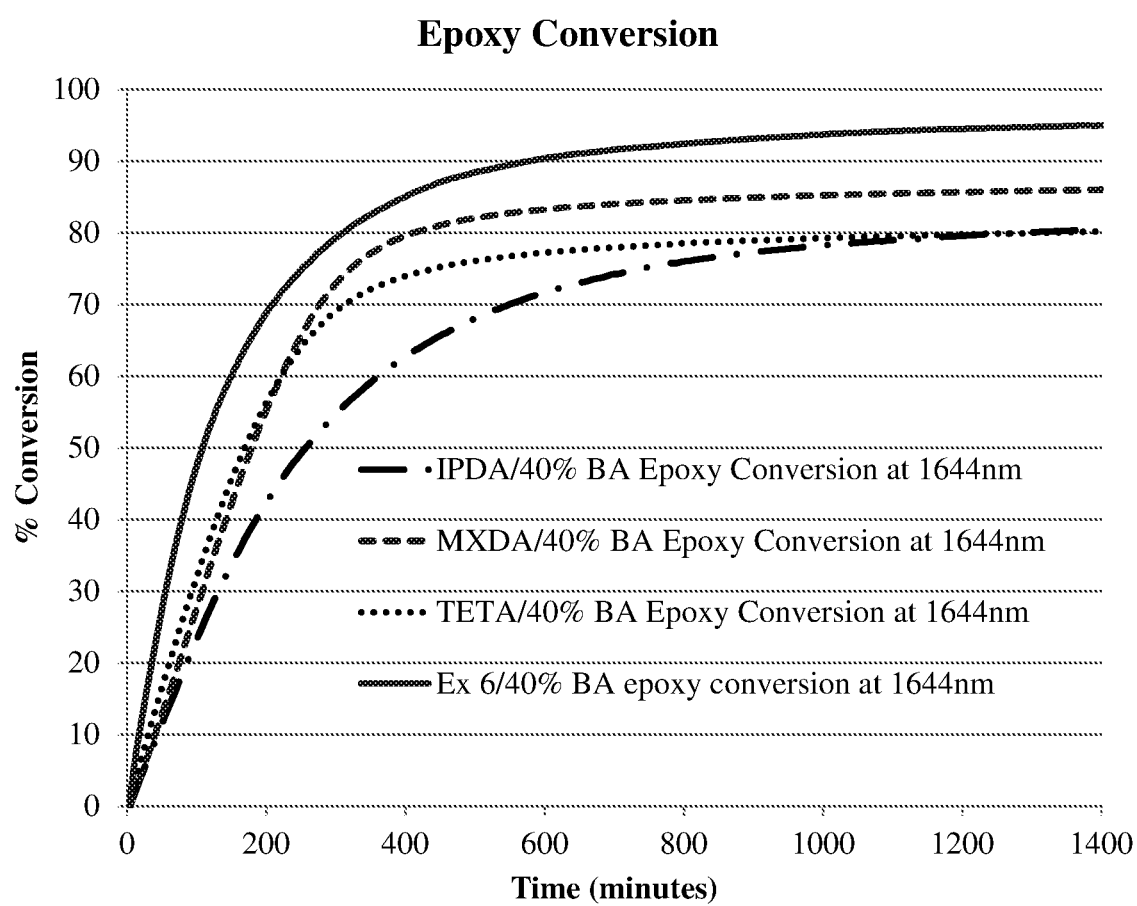
FIG. 1 is a graphical representation showing epoxy conversion determined by near infrared spectroscopy according to exemplary embodiments of the invention and comparative amine-epoxy curing agents.

Provided are amine-epoxy curing agents, amine-epoxy curing compositions and methods for forming cured epoxy. Amine-epoxy curing agents, according to the present invention, are cost effective, provide fast cure at ambient, low and elevated temperatures for epoxy, and are suitable as sole fast curing agent or co-curing agents with other amine epoxy curing agent. Suitable applications include, but are not limited to adhesives, coatings, primers, sealants, curing compounds, construction products, flooring products, and composite products. Further, such coatings, primers, sealants, or curing compounds can be applied to metal or cementitious substrates.

Embodiments of the present invention comprise amine-epoxy curing agents. The amine-epoxy curing agents comprise at least one saturated heterocyclic compound having two nitrogen heteroatoms according to formula (I):

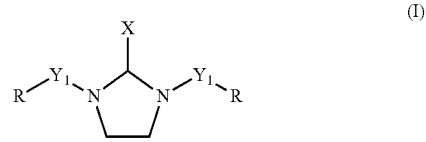

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups. The amine-epoxy curing agents can be used to cure, harden, and/or crosslink multifunctional epoxy resins. The $C_1$ to $C_4$ alkyl groups and the polyethylene polyamine groups having 1 to 8 nitrogen atoms may be branched or unbranched.

Suitable examples for X include hydrogen atom, methyl, ethyl, isopropyl, n-propyl, phenyl, iso-butyl, and n-butyl group. Suitable examples of X include hydrogen atom, methyl, and phenyl group. Other examples of X include hydrogen atom and phenyl, and a particularly suitable example of X is hydrogen atom. Examples of R include hydrogen atom, methyl, ethyl, isopropyl, n-propyl, iso-butyl, n-butyl, 3-methylbutyl, cyclohexyl, and benzyl group. Suitable examples of R include hydrogen atom, methyl, ethyl, isopropyl, iso-butyl, 3-methylbutyl, and benzyl group. Other suitable examples of R include hydrogen atom, methyl, isopropyl, iso-butyl, 3-methylbutyl, and benzyl group, and particularly suitable examples of R are hydrogen atom, methyl, isopropyl, and benzyl group.

Another embodiment of the present invention comprises amine-epoxy curing agents. The amine-epoxy curing agents include at least one saturated heterocyclic compound having two nitrogen heteroatoms according to formula (I) and at least one saturated fused bicyclic heterocyclic compound having three nitrogen heteroatoms according to formula (II):

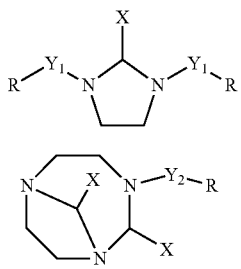

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms or a divalent polyethylene polyamine derivative having 1 to 8 nitrogen atoms, and R is independently a hydrogen atom or a group selected from $C_1$-$C_8$ linear, cyclic, and branched alkyl, alkenyl, and alkaryl groups. The amine-epoxy curing agents can be used to cure, harden, and/or crosslink multifunctional epoxy resins. The $C_1$ to $C_4$ alkyl groups and the polyethylene polyamine groups having 1 to 8 nitrogen atoms may be branched or unbranched.

$Y_1$ and $Y_2$ are divalent polyethylene polyamine groups that include repeating units that may be linear or branched. Suitable repeating divalent polyethylene polyamine group units include the following formula:

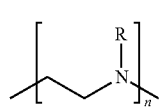

wherein R is independently a hydrogen atom or a group selected from $C_1$-$C_8$ linear, cyclic, and branched alkyl, alkenyl, and alkaryl groups, and R from two consecutive repeating units can form a 5- or 6-member ring with the backbone ethylene unit, and n=1 to 8 for $Y_1$ or n=1 to 7 for $Y_2$.

In one embodiment, the amine-epoxy curing agent comprising at least one saturated heterocyclic compound having two nitrogen heteroatoms according to formula (I) has at least 1 wt %, or at least 5 wt %, or at least 10 wt %, or at least 15 wt %, or at least 20 wt %, or at least 25 wt %, or at least 30 wt %, or at least 35 wt %, or at least 40 wt %, or at least 50%, or at least 60% of the compound represented by formula (I) based on the total weight of the curing agent.

In another embodiment, the amine-epoxy curing agent comprising at least one saturated heterocyclic compound having two nitrogen heteroatoms according to formula (I) and at least one saturated fused bicyclic heterocyclic compound having three nitrogen heteroatoms represented by formula (II) has at least 1 wt %, or at least 5 wt %, or at least 10 wt %, or at least 15 wt %, or at least 20 wt %, or at least 25 wt %, or at least 30 wt %, or at least 35 wt %, or at least 40 wt %, or at least 50%, or at least 60% of the compound represented by formula (I) based on the total weight of the curing agent.

The amine-epoxy curing agent comprising at least one saturated heterocyclic compound having two nitrogen heteroatoms according to formula (I) has a viscosity is in the range from 50 centipoise to 200,000 centipoise at 25° C., or in the range from 100 centipoise to 150,000 centipoise, or from 100 to 100,000 centipoise, or from 100 to 80,000 centipoise, or from 100 to 50,000 centipoise, or from 100 to 30,000 centipoise, or from 100 to 25,000 centipoise, or from 100 to 15,000 centipoise, or from 100 to 10,000 centipoise, or from 100 to 8,000 centipoise, or from 100 to 6,000 centipoise, or from 100 to 5,000 centipoise, or from 100 to 3,000 centipoise, or from 500 centipoise to 150,000 centipoise, or from 500 to 100,000 centipoise, or from 500 to 80,000 centipoise, or from 500 to 50,000 centipoise, or from 500 to 30,000 centipoise, or from 500 to 25,000 centipoise, or from 500 to 15,000 centipoise, or from 500 to 10,000 centipoise, or from 500 to 8,000 centipoise, or from 1,000 centipoise to 150,000 centipoise, or from 1,000 to 100,000 centipoise, or from 1,000 to 80,000 centipoise, or from 1,000 to 50,000 centipoise, or from 1,000 to 30,000 centipoise, or from 1,000 to 25,000 centipoise, or from 1,000 to 15,000 centipoise, or from 1,000 to 10,000 centipoise at 25° C.

In another aspect of the present invention, the amine-epoxy curing agent includes a co-curing agent. The co-curing agent may be an amidoamine curing agent, an aliphatic curing agent, a polyamide curing agent, a cycloaliphatic curing agent, an imidazole, dicyanamide or a Mannich base curing agent which also includes phenalkamines, which are the formaldehyde/amine derivatives of cashew nut shell oil (Cardanol).

In one embodiment, the amine-epoxy curing agent is a reaction product of a $C_1$ to $C_8$ aldehyde and a polyethylene polyamine having 3 to 10 nitrogen atoms, the reaction product includes at least one saturated heterocyclic compound having two nitrogen heteroatoms according to formula (I), above.

In another embodiment, the amine-epoxy curing agent is a reaction product of a $C_1$ to $C_8$ aldehyde and a polyethylene polyamine having 3 to 10 nitrogen atoms, the reaction product includes at least one saturated heterocyclic compound having two nitrogen heteroatoms according to formula (I), above, and at least one saturated fused bicyclic heterocyclic compound having three nitrogen heteroatoms according to formula (II), above.

The polyethylene polyamine compounds having 3 to 10 nitrogen atoms that are useful in producing the amine-epoxy curing agent include a polyethylene polyamine according to formula (IV):

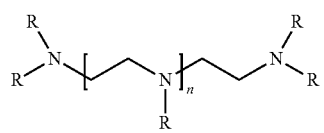

wherein R is independently a hydrogen atom or a group selected from $C_1$-$C_8$ linear, cyclic, and branched alkyl, alkenyl, and alkaryl groups; n is an integer from 1 to 8. Suitable examples of R include hydrogen atom, methyl, isopropyl, and benzyl group. Suitable polyethylene polyamine compounds having 3 to 10 nitrogen atoms according to the present disclosure include, but are not limited to, diethylenetriamine (DETA), triethylenetetramine (TETA), tetraethylenepentamine (TEPA), pentaethylenehexamine (PEHA), and mixtures thereof. Particularly suitable examples of the polyethylene polyamine compounds having 3 to 10 nitrogen atoms include DETA, TETA, and TEPA, and particularly suitable examples are TETA and DETA, and one example, in particular is DETA. Suitable structures for the linear and branched polyethylene polyamine compounds include, but are not limited to the following formulas:

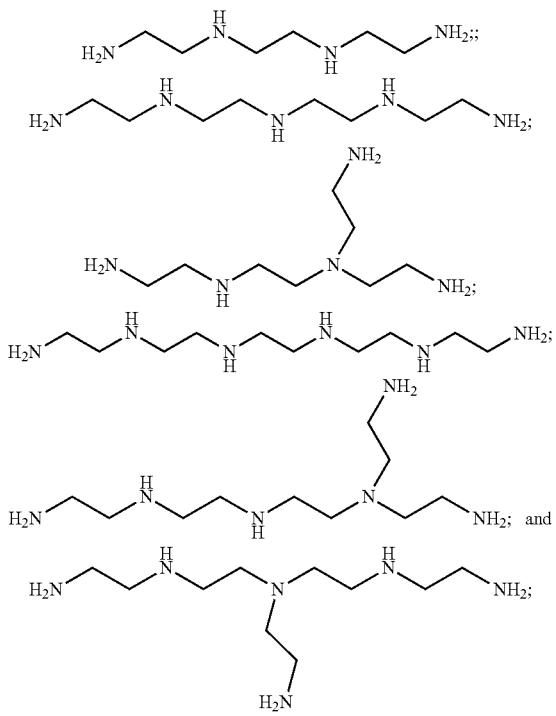

The polyethylene polyamine compounds having 3 to 10 nitrogen atoms be used individually or mixed with one another. It is to be understood that commonly available polyethylene polyamine compounds having 3 to 10 nitrogen atoms such as TETA, TEPA, and PEHA are mixtures of linear and branched isomers and other congeners having cyclic structures. Some of the linear and branched isomers are shown above, these commonly available polyethylene polyamine compounds are included in the definition of polyethylene polyamine compounds of the present disclosure.

The polyethylene polyamine compounds having 3 to 10 nitrogen atoms can be substituted with alkyl groups. Examples include alkylated polyethylene polyamine as disclosed in U.S. Pat. No. 8,518,547 and benzylated polyethylene polyamine polyamine as disclosed in U.S. Pat. Nos. 8,147,964 and 8,168,296. The above referenced patents are hereby incorporated by reference.

The $C_1$ to $C_8$ aldehyde compounds that are useful in producing the amine-epoxy curing agent include but are not limited to, formaldehyde, acetaldehyde, propionaldehyde, and butraldehyde, isobutyraldehyde, trimethylacetaldehyde, 2-methylbutyraldehyde, isovaleraldehyde, valeraldehyde, hexanal, phenylacetaldehyde, benzaldehyde, vanillic aldehyde (also known as vanilline), o-tolualdehyde, o-anisaldehyde, salicylaldehyde and 4-hydroxylbenzaldehyde. Suitable examples of $C_1$ to $C_8$ aldehyde compounds include formaldehyde, acetaldehyde, benzaldehyde, tolualdehyde, o-anisaldehyde, and salicylaldehyde. Other examples of $C_1$ to $C_8$ aldehyde compounds include formaldehyde, and benzaldehyde, and particularly suitable example is formaldehyde. When formaldehyde is used as the $C_1$ to $C_8$ aldehyde compound, it is typically used as an aqueous solution with some methanol as stabilizer for easy handling. For easy handling, the trimer of formaldehyde, 1,3,5-trioxane, and the oligomer and polymer form, paraformaldehyde are used as equivalent to formaldehyde aqueous solution since both are solid. In the present invention, paraformaldehyde is used as equivalent to formaldehyde.

The reaction to form the amine-epoxy curing agent according to the present invention comprises contacting the $C_1$ to $C_8$ aldehyde with the polyethylene polyamine compounds having 3 to 10 nitrogen atoms. The reaction of the $C_1$ to $C_8$ aldehyde and the polyethylene polyamine compounds having 3 to 10 nitrogen atoms may proceed at a reaction temperature of about −20° C. to about 150° C., about 0° C. to about 120° C., about 0° C. to about 100° C., about 0° C. to about 90° C., about 0° C. to about 80° C., about 20° C. to about 100° C., about 20° C. to about 90° C., about 20° C. to about 80° C., about 20° C. to about 70° C. The reaction of the $C_1$ to $C_8$ aldehyde and the polyethylene polyamine compounds is exothermic, thus, cooling might be necessary to maintain reaction temperature at desired range. Water is formed from the reaction of the $C_1$ to $C_8$ aldehyde and the polyethylene polyamine compounds, and is typically removed under designated temperature and pressure. Water from the reaction may be removed at different temperature and pressure than the condition when the reaction of the $C_1$ to $C_8$ aldehyde and the polyethylene polyamine compounds takes place.

The reaction of the $C_1$ to $C_8$ aldehyde and the polyethylene polyamine compounds having 3 to 10 nitrogen atoms to form the amine-epoxy curing agent of the present disclosure may be conducted in a solvent media. Suitable solvent for the reaction includes but is not limited to, water, acetonitrile, alcohol such as methanol, ethanol, n-propanol, isopropanol, n-butanol, Dowanol PM, t-butanol, isobutanol, and benzyl alcohol, and hydrocarbons such as toluene, xylene, hexane, and heptane. Suitable reaction solvent includes water, methanol, ethanol, n-propanol, isopropanol, n-butanol, Dowanol PM and benzyl alcohol. The solvent may be removed after the reaction is complete, or remain as part of the curing agent. For example, benzyl alcohol may remain as plasticizer for the curing agent.

The water formed from the reaction of the $C_1$ to $C_8$ aldehyde and the polyethylene polyamine compounds having 3 to 10 nitrogen atoms may be removed by direct atmosphere distillation or vacuum distillation, or removed by forming azeotropic mixture with a solvent. Azeotropic solvent with water includes, but is not limited to, toluene, xylene, acetonitrile, n-butanol, isobutanol, and t-butanol, heptane, and hexane. Suitable azeotropic solvents include toluene, xylene, acetonitrile, and n-butanol.

In one embodiment, the reaction to form the amine-epoxy curing agent according to the present invention comprises contacting the $C_1$ to $C_8$ aldehyde with the polyethylene polyamine compounds having 3 to 10 nitrogen atoms in a semi-continuous feed process wherein the polyethylene polyamine compounds is charged into the reaction vessel first and then the $C_1$ to $C_8$ aldehyde is continuously fed to the reaction vessel to contact polyethylene polyamine compounds over a period of time at designated temperature and pressure. Water and light components are then removed after the reaction of the $C_1$ to $C_8$ aldehyde and the polyethylene polyamine compounds is complete.

In another embodiment, the reaction to form the amine-epoxy curing agent according to the present invention comprises contacting the $C_1$ to $C_8$ aldehyde with the polyethylene polyamine compounds having 3 to 10 nitrogen atoms in a semi-continuous feed process wherein the polyethylene polyamine compounds is charged into the reaction vessel first and then the $C_1$ to $C_8$ aldehyde is continuously fed to the reaction vessel to contact polyethylene polyamine compounds over a period of time at designated temperature and pressure, and simultaneously, water and light components are removed.

In another embodiment, the reaction to form the amine-epoxy curing agent according to the present invention comprises contacting the $C_1$ to $C_8$ aldehyde with the polyethylene polyamine compounds in a continuous feed process. The $C_1$ to $C_8$ aldehyde and the polyethylene polyamine compounds are fed simultaneously through a tubular reactor such as a static mixer or a heat exchanger or a tube or a column filled with packing or an empty tube where the $C_1$ to $C_8$ aldehyde and the polyethylene polyamine compounds contact and react to form crude product and water. The crude product and water are collected in a receiver vessel. After the feed and reaction is complete, water and light components are removed at designated temperature and pressure.

In yet another embodiment, the reaction to form the amine-epoxy curing agent according to the present invention comprises contacting the $C_1$ to $C_8$ aldehyde with the polyethylene polyamine compounds in a continuous feed process. The $C_1$ to $C_8$ aldehyde and the polyethylene polyamine compounds are fed simultaneously through a tubular reactor such as a static mixer or a heat exchanger or a tube or a column filled with packing or an empty tube where the $C_1$ to $C_8$ aldehyde and the polyethylene polyamine compounds contact and react to form crude product while water and light components are being removed at designated temperature and pressure simultaneously in a receiver vessel where crude product and water from the reaction are collected.

The maximum mole ratio of the $C_1$ to $C_8$ aldehyde to the polyethylene polyamine compounds having 3 to 10 nitrogen atoms is half of the number of amine hydrogen, mathematically expressed below:

$$\left(\frac{\text{number of amine hydrogen}}{2}\right):1$$

The mole ratio of the $C_1$ to $C_8$ aldehyde to the polyethylene polyamine compounds having 3 to 10 nitrogen atoms is at least about 90%, or about 80%, or about 75%, or about 70%, or about 65%, or about 60%, or about 55%, or about 50%, or about 45%, or about 40%, or about 30%, or about 25%, or about 20%, or about 10% of the maximum mole ratio of the $C_1$ to $C_8$ aldehyde to the polyethylene polyamine compounds having 3 to 10 nitrogen atom to 1.

The present invention also comprises amine-epoxy curing agent compositions and methods of making these compositions. A curing agent composition in accordance with the present invention can be used to cure, harden, and/or cross-link an epoxy resin. Such curing agent composition comprises at least one saturated heterocyclic compound having two nitrogen heteroatoms according to formula (I).

In another aspect, such curing agent composition comprises at least one saturated heterocyclic compound having two nitrogen heteroatoms according to formula (I) and at least one saturated fused bicyclic heterocyclic compound having three nitrogen heteroatoms according to formula (II).

Generally, the curing agent composition has an amine hydrogen equivalent weight (AHEW) based on 100% solids from about 30 to about 500. Further, the curing agent composition can have an AHEW based on 100% solids from about 60 to about 400, or from about 80 to about 300, or from about 40 to about 200, or from about 55 to about 450, or from about 40 to about 150, or from about 70 to about 350, or from about 90 to about 250, or from about 100 to about 200, or from about 30 to about 400, or from about 30 to about 300, or from about 30 to about 250, or from about 30 to about 200, or from about 35 to about 400, or from about 35 to about 300, or from about 35 to about 250, or from about 35 to about 200.

In another aspect, the present invention comprises a curing agent composition comprising the contact product of:
(i) an amine-epoxy curing agent comprising at least one saturated heterocyclic compound having two nitrogen heteroatoms according to formula (I) and
(ii) at least one multifunctional amine having three or more active amine hydrogens.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions or formulations described herein. Still further, two or more of the components of the contact product may react to form other components composing the composition. Combining additional materials or components can be done by any method known to one of ordinary skill in the art.

In another aspect, the present invention comprises a curing agent composition comprising the contact product of:
(i) an amine-epoxy curing agent including at least one saturated heterocyclic compound having two nitrogen heteroatoms according to formula (I) and at least one saturated fused bicyclic heterocyclic compound having three nitrogen heteroatoms according to formula (II), and
(ii) at least one multifunctional amine having three or more active amine hydrogens.

Additionally, curing agent compositions described herein can be solvent-based. Alternatively, in another aspect of the present invention, these compositions can further comprise at least one diluent, such as, for example, an organic solvent, or an organic or inorganic acid. Appropriate organic solvents are well known to those skilled in the art of amine formulation chemistry. Exemplary organic solvents suitable for use in the present disclosure include, but are not limited to, benzyl alcohol, butanol, toluene, xylene, methyl ethyl ketone, and the like, or combinations thereof. Non-limiting examples of organic and inorganic acids are acetic acid, sulfamic acid, lactic acid, salicylic acid, sebacic acid, boric acid, phosphoric acid, p-toluene sulfonic acid, trifluoroacetic acid, and the like, or combinations thereof. Such acids can increase the curing speed of the curing agent composition.

The curing agent compositions also can be further modified with monofunctional epoxides, such as, for example, phenyl glycidyl ether, o-cresyl glycidyl ether, p-tert-butyl-phenyl glycidyl ether, n-butyl glycidyl ether, and other similar glycidyl ethers or esters. Further, curing agent compositions disclosed herein can be blended with other commercially available curing agents. Such commercially available curing agents include, but are not limited to, solvent based, solvent free or water-based curing agents, which can be employed in a blend to target specific properties, such as cure rate, drying speed, hardness development, clarity, and gloss.

Curing agent compositions in accordance with the present invention can further comprise at least one multifunctional amine. Multifunctional amine, as used herein, describes compounds with amine functionality and which contain three (3) or more active amine hydrogens.

Non-limiting examples of multifunctional amines having three (3) or more active amine hydrogens that are within the scope of the present disclosure include, but are not limited to, an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a diglycidyl ether of bisphenol A or bisphenol F or an epoxy novolac resin, or a mono-glycidyl ether of a hydric phenol compound or an alcohol, and the like, or any combination thereof.

More than one multifunctional amine can be used in the compositions of the present disclosure. For example, the at least one multifunctional amine can comprise an aliphatic amine and a Mannich base derivative of a cycloaliphatic amine. Also, the at least one multifunctional amine can comprise one aliphatic amine and one different aliphatic amine.

Exemplary aliphatic amines include polyethyleneamines (EDA, DETA, TETA, TEPA, PEHA, and the like), polypropyleneamines, aminopropylated ethylenediamines (Am3, Am4, Am5, and the like), aminopropylated propylenediamines, 1,6-hexanediamine, 3,3,5-trimethyl-1,6-hexanediamine, 3,5,5-trimethyl-1,6-hexanediamine, 2-methyl-1,5-pentanediamine, and the like, or combinations thereof. In one aspect of this invention, the at least one multifunctional amine is EDA, DETA, TETA, TEPA, PEHA, propylenediamine, dipropylenetriamine, tripropylenetetramine, N-3-aminopropyl ethylenediamine (Am3), N,N'-bis(3-aminopropyl) ethylenediamine (Am4), N,N,N'-tris(3-aminopropyl) ethylenediamine (Am5), N-3-aminopropyl-1,3-diaminopropane, N,N'-bis(3-aminopropyl)-1,3-diaminopropane, N,N,N'-tris(3-aminopropyl)-1,3-diaminopropane, or any combination thereof. Additionally, the poly(alkylene oxide) diamines and triamines commercially available under the JEFFAMINE® trademark from Huntsman Corporation, are useful in the present invention. Illustrative examples include, but are not limited to, JEFFAMINE® D-230, JEFFAMINE® D-400, JEFFAMINE® D-2000, JEFFAMINE® D-4000, JEFFAMINE® T-403, JEFFAMINE® EDR-148, JEFFAMINE® EDR-192, JEFFAMINE® C-346, JEFFAMINE® ED-600, JEFFAMINE® ED-900, JEFFAMINE® ED-2001, and the like, or combinations thereof. Cycloaliphatic and aromatic amines include, but are not limited to, 1,2-diaminocyclohexane, 1,3-diaminocyclohexane, 1,4-diaminocyclohexane, aminopropylcyclohexylamine (APCHA), hydrogenated ortho-toluenediamine, hydrogenated meta-toluenediamine, metaxylylene diamine, hydrogenated metaxylylene diamine (referred to commercially as 1,3-BAC), isophorone diamine, norbornane diamines, 3,3'-dimethyl-4,4'-diaminodicyclohexyl methane, 4,4'-diaminodicyclohexyl methane, 2,4'-diaminodicyclohexyl methane, a mixture of methylene bridged poly(cyclohexyl-aromatic) amines, and the like, or combinations thereof. The mixture of methylene bridged poly(cyclohexyl-aromatic)amines is abbreviated as either MBPCAA or MPCA, and is described in U.S. Pat. No. 5,280,091, which is incorporated herein by reference in its entirety. In one aspect of the present disclosure, the at least one multifunctional amine is a mixture of methylene bridged poly(cyclohexyl-aromatic)amines (MPCA).

Mannich base derivatives can be made by the reaction of the above described aliphatic amines, cycloaliphatic amines, or aromatic amines with phenol or a substituted phenol and formaldehyde. An exemplary substituted phenol used to make Mannich bases with utility in the present disclosure is cardanol, which is obtained from cashew nut shell liquid. Alternatively, Mannich bases can be prepared by an exchange reaction of a multifunctional amine with a tertiary amine containing a Mannich base, such as tris-dimethylaminomethylphenol (commercially available as ANCAMINE® K-54 from Air Products and Chemicals, Inc.) or bis-dimethylaminomethylphenol. Polyamide derivatives can be prepared by the reaction of an aliphatic amine, cycloaliphatic amine, or aromatic amine with dimer fatty acid, or mixtures of a dimer fatty acid and a fatty acid. Amidoamine derivatives can be prepared by the reaction of an aliphatic amine, cycloaliphatic amine, or aromatic amine with fatty acids. Amine adducts can be prepared by the reaction of an aliphatic amine, cycloaliphatic amine, or aromatic amine with an epoxy resin, for example, with the diglycidyl ether of bisphenol-A, the diglycidyl ether of bisphenol-F, or epoxy novolac resins. The aliphatic, cycloaliphatic, and aromatic amines also can be adducted with monofunctional epoxy resins, such as phenyl glycidyl ether, cresyl glycidyl ether, butyl glycidyl ether, other alkyl glycidyl ethers, and the like.

Embodiments of the present invention comprises amine-epoxy compositions. The amine-epoxy compositions comprise an amine-epoxy curing agent and at least one multifunctional epoxy resin. For example, an amine-epoxy composition, in accordance with the present invention, comprises A) the reaction product of the $C_1$ to $C_8$ aldehyde and the polyethylene polyamine compounds having 3 to 10 nitrogen atoms; and B) an epoxy composition comprising at least one multifunctional epoxy resin. Optionally, various additives can be present in the compositions or formulations used to produce fabricated articles, dependent upon the desired properties. These additives can include, but are not limited to, solvents (including water), accelerators, plasticizers, fillers, fibers such as glass or carbon fibers, pigments, pigment dispersing agents, rheology modifiers, thixotropes In yet another aspect of this invention, a method for forming cured epoxy includes reacting an amine epoxy curing agent with at least one multifunctional epoxy resin.

Amine-epoxy compositions of the present invention comprise the reaction product of a curing agent composition and an epoxy composition comprising at least one multifunctional epoxy resin. Multifunctional epoxy resin, as used herein, describes compounds containing 2 or more 1,2-epoxy groups per molecule. Epoxide compounds of this type are well known to those skilled in the art and are described in Y. Tanaka, "Synthesis and Characteristics of Epoxides", in C. A. May, ed., *Epoxy Resins Chemistry and Technology* (Marcel Dekker, 1988), which is incorporated herein by reference in its entirety.

The relative amount chosen for the epoxy composition versus that of the curing agent composition, or hardener, can vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition, can result in coatings which have increased drying time, but with increased hardness and improved appearance as measured by gloss. Amine-epoxy compositions of the present disclosure generally have stoichiometric ratios of epoxy groups in the epoxy composition to amine hydrogens in the curing agent composition ranging from about 1.5:1 to about 0.7:1. For example, such amine-epoxy compositions can have stoichiometric ratios of epoxy to amine hydrogen about 1.5:1, about 1.4:1, about 1.3:1, about 1.2:1, about 1.1:1, about 1:1, about 0.9:1, about 0.8:1, or about 0.7:1. In another aspect, the stoichiometric ratio ranges from about 1.3:1 to about 0.7:1. In yet another aspect, the stoichiometric ratio ranges from about 1.2:1 to about 0.8:1. In still another aspect, the stoichiometric ratio ranges from about 1.1:1 to about 0.9:1.

One class of epoxy resins suitable for use in the present invention comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

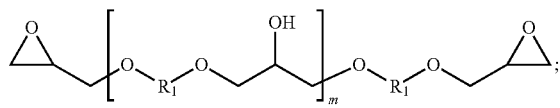

where m is an integer, and R$_1$ is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of dihydric phenol. While in any given molecule the value of m is an integer, the materials are invariably mixtures which can be characterized by an average value of m, which is not necessarily a whole number. Polymeric materials with an average value of m between 0 and about 7 can be used in one aspect of the present disclosure.

In another aspect, epoxy novolac resins, which are the glycidyl ethers of novolac resins, can be used as multifunctional epoxy resins in accordance with the present disclosure. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to 3000 or more. Because these products are solid at room temperature, they are often referred to as solid epoxy resins.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature. Generally, multifunctional resins with EEW's based on solids of about 160 to about 750 are useful in the prevent invention. In another aspect the multifunctional epoxy resin has an EEW in a range from about 170 to about 250.

Depending upon the end-use application, it can be beneficial to reduce the viscosity of the compositions of the present invention by modifying the epoxy component. For example, the viscosity can be reduced to allow an increase in the level of pigment in a formulation or composition while still permitting easy application, or to allow the use of a higher molecular weight epoxy resin. Thus, it is within the scope of the present invention for the epoxy component, which comprises at least one multifunctional epoxy resin, to further comprise a monofunctional epoxide. Examples of monoepoxides include, but are not limited to, styrene oxide, cyclohexene oxide, ethylene oxide, propylene oxide, butylene oxide, and the glycidyl ethers of phenol, cresols, tert-butylphenol, other alkyl phenols, butanol, 2-ethylhexanol, C$_4$ to C$_{14}$ alcohols, and the like, or combinations thereof. The multifunctional epoxy resin can also be present in a solution or emulsion, with the diluent being water, an organic solvent, or a mixture thereof.

Compositions of the present invention can be used to produce various articles of manufacture. Depending on the requirements during the manufacturing of or for the end-use application of the article, various additives can be employed in the formulations and compositions to tailor specific properties. These additives include, but are not limited to, solvents (including water), accelerators, plasticizers, fillers, fibers such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art can be included in the compositions or formulations and are within the scope of the present invention.

The present invention also is directed to articles of manufacture comprising the compositions disclosed herein. For example, an article can comprise an amine-epoxy composition which comprises the reaction product of a curing agent composition and an epoxy composition. Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds can be applied to metal or cementitious substrates. Coatings based on these amine-epoxy compositions can be solvent-free or can contain diluents, such as water or organic solvents, as needed for the particular application. Coatings can contain various types and levels of pigments for use in paint and primer applications. Amine-epoxy coating compositions comprise a layer having a thickness ranging from 40 to 400 μm (micrometer), preferably 80 to 300 μm, more preferably 100 to 250 μm, for use in a protective coating applied on to metal substrates. In addition, for use in a flooring product or a construction product, coating compositions comprise a layer having a thickness ranging from 50 to 10,000 μm, depending on the type of product and the required end-properties. A coating product that delivers limited mechanical and chemical resistances comprises a layer having a thickness ranging from 50 to 500 μm, preferably 100 to 300 μm; whereas a coating product such as, for example, a self-leveling floor that delivers high mechanical and chemical resistances comprises a layer having a thickness ranging from 1,000 to 10,000 µm, preferably 1,500 to 5,000 µm.

Numerous substrates are suitable for the application of coatings of the present invention with proper surface preparation, as is well known to one of ordinary skill in the art. Such substrates include, but are not limited to, concrete and various types of metals and alloys, such as steel and aluminum. Coatings of the present invention are suitable for the painting or coating of large metal objects or cementitious substrates including ships, bridges, industrial plants and equipment, and floors.

Coatings of this invention can be applied by any number of techniques including spray, brush, roller, paint mitt, and the like. In order to apply very high solids content or 100% solids coatings of the present disclosure, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present invention in combination with concrete or other materials commonly used in the construction industry. Applications of compositions of the present invention include, but are not limited to composition's use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present disclosure can be applied to surfaces to improve adhesive bonding prior to the application of a coating. As it pertains to concrete and cementitious application, a coating is an agent used for application on a surface to create a protective or decorative layer or a coat. Crack injection and crack filling products also can be prepared from the compositions disclosed herein. Amine-epoxy compositions of the present invention can be mixed with cementitious materials such as concrete mix to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the present invention these curing agent compositions will have applicability in making epoxy filament-wound tanks, infusion composites such as windmill blades, aerospace adhesives, industrial adhesives, as well as other related applications. A composite is a material made of different substances, and in the case of resin technologies, composites refer to resin impregnated systems where the resin is reinforced by the addition of reinforcing materials such as fillers and fibers for improving general properties of the resulting product. These materials work together but are not soluble in one another. In the present case, the binder component comprises the epoxy resin and epoxy curing agent(s). There are many types of composite applications such as prepegs, laminates, filament windings, braiding, pultrusion, wet lay and infusion composites. Resin infusion, or resin transfer, is a process by which resin is introduced to the composite mold, the reinforcement material having already been placed into the mold and closed prior to resin introduction. There are variations on this process such as those that are vacuum assisted or transfer resin under (high) pressure The uses of epoxy resins which are cured, hardened, and/or crosslinked with amine-based curing agents are well known. These amine-epoxy materials are widely used in applications ranging from coatings, where they can be used in various applications such as primers, tie-coats, and finishes. They can be applied on many substrates. They can be used in laminates, adhesives, floorings, dust free finishes, secondary containment, linings, reinforcement, repair formulations, tooling, potting, and casting. They can be used in many industries like building (food manufacture, bridges, sewage plants), automotive, marine applications (ship painting, buoy painting, shipping containers), aeronautic (gluing of parts, honeycomb reinforcement for cabin structure, re-entry shield for satellites), electronic (printed circuit base, potting of electronic components, wire insulation), sports (tennis rackets, golf clubs, canoes, skis) and many mores applications such as filament winding for containers and tanks, laminates for wind energy and propellers for planes, syntactic foams and many other applications which are well known to those skilled in the art.

The present invention also includes articles of manufacture comprising an amine-epoxy composition as described above. Such articles can include, but are not limited to, an adhesive, a coating, a primer, a sealant, a curing compound, a construction product, a flooring product, a composite product, laminate, potting compounds, grouts, fillers, cementitious grouts, or self-leveling flooring. Additional components or additives can be used together with the compositions of the present invention to produce articles of manufacture. Further, such coatings, primers, sealants, curing compounds or grouts can be applied to metal or cementitious substrates.

The invention is further illustrated by the following examples, which are not to be construed as imposing limitations to the scope of this invention. Various other aspects, embodiment, modifications, and equivalents thereof which, after reading the description herein, may suggest themselves to one of ordinary skill in the art without departing from the spirit of the present disclosure or the scope of the appended claims.

EXAMPLES

The following synthesis examples are provided to illustrate certain aspects or embodiments of the instant invention and shall not limit the scope of the claims appended hereto.

Synthesis Examples

Diethylenetiamine (DETA), formaldehyde aqueous solution were purchase from Aldrich. The reaction product was analyzed by gas chromatography (GC) to determine the amount of unreacted DETA, Metrohm titrator using Karl Fisher titration method for residual water content, Brookfield viscometer for viscosity, Metrohm titrator for amine value, and nuclear magnetic resonance (NMR) for chemical composition. The NMR experiments were performed at ambient temperature employing the Bruker DRX-400 FT-NMR spectrometer equipped with a 10 mm BBO probe. Quantitative $^{13}C$ NMR data was acquired using inverse-gated decoupling, a 45° pulse, and a 6 second relaxation delay. The samples were dissolved in chloroform-d with chromium acetylacetonate added as a relaxation agent. The chemical shift scale was referenced to the solvent peak. GC analysis was performed on Agilent 7890 Gas Chromatograph equipped with a Agilent CP-Volamine 0.32 mm×30 m—column and a Flame Ionization Detector. The samples were prepared as 1% solutions in isopropanol then placed in 2 mL autosampler vials for GC analysis. Standard solutions ranging from 0.005 to 0.51 wt % DETA in isopropanol were used to create six point external, linear calibration curve to quantify the residual DETA in the samples. The square of correlation coefficient ($R^2$) value for the calibration curves are 0.999.

Example 1 Synthesis of Reaction Product of DETA with Formaldehyde at Molar Ratio of 1.25:1 Formaldehyde to DETA DETA (250 g, 2.4 mol) was charge to a reactor equipped with a nitrogen inlet, a condenser, an addition funnel, and an overhead stirrer. To DETA was added formaldehyde aqueous solution (245.6 g, 3.0 mol) via an addition funnel to maintain temperature below 60° C. After the addition, the reaction was kept at 60° C. for 30 minutes. Water was then removed under reduced pressure. The product was obtained as a clear liquid in quantitative yield with amine value of 927 meqKOH/g, viscosity of 347 mPa·s at 25° C., water content of 0.41%, and residual DETA of 5.7%. NMR analysis showed that 57 mol % of DETA formed 1-(2-aminoethyl)imidazolidine, which corresponds to 56 wt % to the total weight in the product by calculation.

Example 2 Synthesis of Reaction Product of DETA with Formaldehyde at Molar Ratio of 1:1 Formaldehyde to DETA Example 2 utilized the same process as described in Example 1. The product was obtained as a clear liquid in quantitative yield with amine value of 960 meqKOH/g, viscosity of 71 mPa·s at 25° C. and residual DETA of 13.5%. NMR analysis showed that 61 mol % of DETA formed 1-(2-aminoethyl)imidazolidine, which corresponds to 70 wt % to the total weight in the product by calculation.

Example 3 Synthesis of Reaction Product of DETA with Formaldehyde at Molar Ratio of 1.35:1 Formaldehyde to DETA Example 3 utilized the same process as described in Example 1. The product was obtained as a clear liquid in quantitative yield with amine value of 915 meqKOH/g, viscosity of 750 mPa·s at 25° C. and water content of 0.48%. NMR analysis showed that 46 mol % of DETA formed 1-(2-aminoethyl)imidazolidine, which corresponds to 44 wt % to the total weight in the product by calculation.

Example 4 Synthesis of Reaction Product of DETA with Formaldehyde at Molar Ratio of 1.55:1 Formaldehyde to DETA Example 4 utilized the same process as described in Example 1. The product was obtained as a clear liquid in quantitative yield with amine value of 859 meqKOH/g, viscosity of 5024 mPa·s at 25° C. and residual DETA of 1.9%. NMR analysis showed that 45 mol % of DETA formed 1-(2-aminoethyl)imidazolidine, which corresponds to 43 wt % to the total weight in the product by calculation.

Example 5 Synthesis of Reaction Product of DETA with Formaldehyde at Molar Ratio of 1.60:1 Formaldehyde to DETA Example 5 utilized the same process as described in Example 1. The product was obtained as a clear liquid in quantitative yield with amine value of 857 meqKOH/g, viscosity of 9470 mPa·s at 25° C. and residual DETA of 1.3%. NMR analysis showed that 39 mol % of DETA formed 1-(2-aminoethyl)imidazolidine, which corresponds to 37 wt % to the total weight in the product by calculation.

Example 6 Synthesis of Reaction Product of DETA with Formaldehyde at Molar Ratio of 1.65:1 Formaldehyde to DETA Example 6 utilized the same process as described in Example 1. The product was obtained as a clear liquid in quantitative yield with amine value of 855 meqKOH/g, viscosity of 19450 mPa·s at 25° C. and residual DETA of 1.2%. NMR analysis showed that 36 mol % of DETA formed 1-(2-aminoethyl)imidazolidine, which corresponds to 34 wt % to the total weight in the product by calculation.

Example 7 Synthesis of Reaction Product of DETA with Formaldehyde at Molar Ratio of 1.70:1 Formaldehyde to DETA Example 7 utilized the same process as described in Example 1. The product was obtained as a clear liquid in quantitative yield with amine value of 879 meqKOH/g, viscosity of 29000 mPa·s at 25° C. and residual DETA of 1.0%. NMR analysis showed that 36 mol % of DETA formed 1-(2-aminoethyl)imidazolidine, which corresponds to 34 wt % to the total weight in the product by calculation.

Example 8 Synthesis of Reaction Product of DETA with Formaldehyde at Molar Ratio of 1.70:1 Formaldehyde to DETA Example 8 utilized a modified process as described in Example 1. DETA was charged to reactor and heated to 60° C., and formaldehyde aqueous solution was added. After addition, the reaction was heated to 90° C. for 1 hour. The product was obtained as a clear liquid in quantitative yield with amine value of 880 meqKOH/g, viscosity of 33890 mPa·s at 25° C., and residual DETA of 0.97%. NMR analysis showed that 38 mol % of DETA formed 1-(2-aminoethyl)imidazolidine, which corresponds to 35 wt % to the total weight in the product by calculation.

Example 9 Synthesis of Reaction Product of DETA with Formaldehyde at Molar Ratio of 1.70:1 Formaldehyde to DETA Example 9 utilized a modified process as described in Example 1. Isopropyl alcohol at an amount equal to half of the weight of DETA was charged to reactor to reactor and heated to 60° C. DETA and formaldehyde aqueous solution was added simultaneously. After addition, the reaction was heated to 80° C. for 1 hour. The product was obtained as a clear liquid in quantitative yield with amine value of 881 meqKOH/g, viscosity of 36410 mPa·s at 25° C., and residual DETA of 0.86%. NMR analysis showed that 34 mol % of DETA formed 1-(2-aminoethyl)imidazolidine, which corresponds to 32 wt % to the total weight in the product by calculation.

Example 10 Synthesis of Reaction Product of DETA with Formaldehyde at Molar Ratio of 1.60:1 Formaldehyde to DETA DETA and formaldehyde aqueous solution were fed to the inlet of a 0.25 inch OD stainless steel static mixer made by Koflo simultaneously over a course of 3 hours. The static mixer was not insulated. The effluent from the static mixer was accumulated in an agitated stainless steel reactor maintained at 55° C. Water was then removed under reduced pressure. The product was obtained as a clear liquid in quantitative yield with amine value of 874 meqKOH/g, viscosity of 8050 mPa·s at 25° C., and water content of 0.33%. NMR analysis showed that 38 mol % of DETA formed 1-(2-aminoethyl)imidazolidine, which corresponds to 36 wt % to the total weight in the product by calculation.

Example 11 Synthesis of Reaction Product of DETA with Formaldehyde at Molar Ratio of 1.70:1 Formaldehyde to DETA at Low Temperature in Isopropyl Alcohol DETA (200.0 g, 1.9 mol) and isopropyl alcohol at an amount equal to the weight of DETA (200 g) were charged to the reactor. The solution was cooled down to 0° C. with an ice bath. To the solution was added formaldehyde aqueous solution (267.1 g, 3.3 mol) to maintain temperature below room temperature of 25° C. After the addition, the reaction was warmed up to room temperature in 1 hour. Water and solvent were then removed under reduced pressure. The product was obtained as a clear liquid in quantitative yield with amine value of 899 meqKOH/g, viscosity of 16100 mPa·s at 25° C., water content of 0.12%, and residual DETA of 2.0%. NMR analysis showed that 39 mol % of DETA formed 1-(2-aminoethyl)imidazolidine, which corresponds to 36 wt % to the total weight in the product by calculation.

Example 12 Synthesis of Reaction Product of DETA with Formaldehyde at Molar Ratio of 1.70:1 Formaldehyde to DETA at Low Temperature in Water and Methanol Example 12 utilized the same process as described in Example 11 except 15% of water and 15% of methanol to the weight of DETA were used instead of isopropyl alcohol in an amount equal to the weight of DETA. The product was obtained as a clear liquid in quantitative yield with amine value of 839 meqKOH/g, viscosity of 13570 mPa·s at 25° C., water content of 0.20%, and residual DETA of 0.7%. NMR analysis showed that 43 mol % of DETA formed 1-(2-aminoethyl)imidazolidine, which corresponds to 40 wt % to the total weight in the product by calculation.

Example 13 Synthesis of Reaction Product of TETA with Formaldehyde at Molar Ratio of 1.50:1 Formaldehyde to TETA Example 13 utilized the same process as described in Example 1. The product was obtained as a clear liquid in quantitative yield with amine value of 851 meqKOH/g, viscosity of 5640 mPa·s at 25° C., water content of 1.0%. NMR analysis showed that 51 mol % of TETA formed imidazolidine attached at the terminal of the molecules.

Example 14 Synthesis of Reaction Product of DETA with Formaldehyde at Molar Ratio of 1.45:1 Formaldehyde to DETA Example 14 utilized the same process as described in Example 1. The product was obtained as a clear liquid in quantitative yield with amine value of 914 meqKOH/g, viscosity of 2493 MPA·S at 25° C.

Example 15 Synthesis of Reaction Product of PEHA with Formaldehyde at Molar Ratio of 2.0:1 Formaldehyde to PEHA Example 15 utilized the same process as described in Example 11 except 50% of ethanol to the weight of PEHA was used. The product was obtained as a viscous light brown liquid in quantitative yield with amine value of 810 meqKOH/g, viscosity of 153600 mPa·s at 25° C., water content of 1.0%. NMR analysis showed that 31 mol % of PEHA formed imidazolidine attached at the terminal of the molecules.

Example 16 Synthesis of Reaction Product of Benzylated DETA/TETA with Formaldehyde at Molar Ratio of 1.0:1 Formaldehyde to Benzylated DETA/TETA Benzylated DETA/TETA was synthesized according to U.S. Pat. No. 8,143,331, Example 10; the disclosure of which is hereby incorporated by reference.

The process for synthesis of reaction product of benzylated DETA/TETA with formaldehyde is the same as described in Example 1. Benzylated DETA/TETA (223.0 g, 1.0 mol) was reacted with formaldehyde aqueous solution (81 g, 1.0 mol). The product was obtained as a clear liquid in quantitative yield with amine value of 507 meqKOH/g, viscosity of 67 mPa·s at 25° C. NMR analysis showed that 18 mol % of imidazolidine was attached at the terminal of the molecules.

Example 17 Synthesis of Reaction Product of DETA with Formaldehyde at Molar Ratio of 1.6:1 Formaldehyde to DETA Using 1-Butanol as Azeotropic Solvent to Remove Water Example 17 utilized the same process as described in Example 1 except water was removed by azeotropic distillation with butanol. After 80% of the expected amount of water was distilled, 1-butanol at an amount equal to 20% of the expected amount of water was added to the reactor. The solvent and water removal process was continued until no more condensate was collected. The product was obtained as clear liquid, with amine value of 873 meq KOH/g, water content of <0.1%, and viscosity of 8900 mPa·s at 25° C.

Example 18 Synthesis of Reaction Product of DETA with Paraformaldehyde at Molar Ratio of 1.7:1 Paraformaldehyde to DETA Example 18 utilized the same process as described in Example 1 except paraformaldehyde was used instead of formaldehyde aqueous solution. Paraformaldehyde was added as solid in portions to DETA. The product was obtained as a clear light yellow liquid in quantitative yield with amine value of 908 meqKOH/g, viscosity of 10480 mPa·s at 25° C., and residual DETA of 1%. NMR analysis showed that 44 mol % of DETA formed 1-(2-aminoethyl) imidazolidine, which corresponds to 41 wt % to the total weight in the product by calculation.

Testing of Curing Agents

Formulated mixtures were prepared by combining and mixing the components given in examples 1-18. with a standard bisphenol-A based epoxy resin (DGEBA, e.g Epon 828, ex-Hexion, epoxy equivalent weight, EEW 190). Mixing was conducted using an amine:epoxy resin stoichiometric ratio of 1:1, unless otherwise specified. MXDA (m-xylenediamine), IPDA (isophorondiamine) were purchased from Aldrich, Ancamine® AEP (N-aminoethylpiperazine), Ancamine® TETA, Ancamine® 1638 (A1638), Ancamine® 1618 (A1618), Ancamine® 2143 (A2143), Ancamine® 1856, Ancamine® 2609W, Sunmide CX-1151, Ancamide® 350A (A350A), Ancamide 2050 (A2050), Amicure® PACM, and Ancamine® 2432 (A2432) were obtained from Air Products and Chemicals, Inc. The inventive examples, and MXDA, IPDA, AEP, and TETA of the comparative examples were prepared in 40% benzyl alcohol unless specified otherwise. Ancamine® and Ancamide® curing agents were used as received. The test methods are outlined in Table 1.

TABLE 1

General Test Methods

| Property | Measurements | ASTM METHOD |
|---|---|---|
| Gel time | 150 gram sample | D2471 |
| Drying time | BK recorder Thin film set times Phase 1: set to touch Phase 2: tack free Phase 3: dry hard Phase 4: dry through | D5895 |
| Film Appearance | Gloss (20°)/gloss (60°) | D523 |
| Solvent Resistance | MEK Double Rubs | D7835/ D7835M |
| Hardness | Persoz Pendulum Hardness (s) Shore D | D4366 D2240 |
| Yellowness | Yellowness Index, Delta Yellowness Index | E313-96 |
| Mechanical performance | Tensile strength | D638 Type I |

TABLE 1-continued

General Test Methods

| Property | Measurements | ASTM METHOD |
|---|---|---|
| Adhesion | Cross hatch adhesion test | D3359 |
| Peak temperature of cure | Dynamic DSC first scan | |
| Degree of cure | Dynamic DSC first scan after cure | |
| Initial mix viscosity | Rotational rheometry at elevated temperature | |
| Initial viscosity build-up | Rotational rheometry at elevated temperature (time to 200 mPa · s) | |
| Final viscosity build-up | Oscillating rheometry at elevated temperature (time to gel point G' = G") | |
| Thermal resistance (Tg) | Dynamic DSC second scan | |

Test Example 1: Gel Time of Curing Agents

Table 2 shows the gel time of the inventive examples in comparison with known curing agents. Ancamine® 1638 is a fast curing agent of modified aliphatic amine based on DETA-epoxy adduct, and Ancamine® 2432 is a modified amine curing agent based on MXDA Mannich base with fast cure speed.

The gel time characterizes the time a composition transitions from a liquid to a gel. The gel time of the amine-epoxy compositions was measured with a TECHNE gelation timer model FGT 6 using ASTM D2471. One end of the metal rod was connected to the TECHNE gelation timer and the other end with the 22 mm diameter stainless steel plunger. A total of 150 grams of the mixture comprising the liquid amine curing agent composition was mixed stoichiometrically and with the epoxy resin Epon 828 for 2-3 minutes in an 8 oz plastic jar at 25° C. The gelation timer was turned to "start/hold" when the mixing started to start the timer. After mixing, the stainless steel plunger was immersed into epoxy-liquid curing agent mixture and gel timer was turned to "start/operate". Gel time was recorded in minutes at 25° C.

The gel time data in Table 2 clearly indicated that curing agent compositions of the present disclosure containing the reaction product of polyethylene polyamine with aldehyde cured fast in comparison with known curing agents of aliphatic, cycloaliphatic and Mannich base.

TABLE 2

Gel time of epoxy amine curing agent composition

Inventive examples

| New Curing agents | Ex 1 | Ex 2 | Ex 3 | Ex 4 | Ex 5 | Ex 6 | Ex 11 | Ex 13 | Ex 14 | Ex 15 |
|---|---|---|---|---|---|---|---|---|---|---|
| PHR | 34 | 41 | 46 | 56 | 60 | 63 | 68 | 48 | 50 | 57 |
| Gel time (min.) | 18.9 | 19.2 | 17.2 | 16.6 | 16.4 | 15.8 | 10.9 | 16.8 | 18.8 | 20.6 |

Comparative examples

| Curing agents | Ex 11 | DETA | AEP | IPDA | TETA | MXDA | A1638 | A2432 |
|---|---|---|---|---|---|---|---|---|
| PHR | 68 | 18 | 38 | 37 | 21 | 30 | 16 | 46 |
| Gel time (min.) | 10.9 | 20.4 | 8.2 | 32.4 | 18.6 | 29.8 | 15 | 27 |

Test Example 2: Thin Film Set Times of the Clear Coatings

The dry time or thin film set time (TFST) was determined using a Beck-Koller recorder, in accordance with ASTM D5895. The amine-epoxy coatings were prepared on standard glass panels at a wet film thickness of about 75 micron WFT (wet film thickness) using a Bird applicator resulting in dry film thicknesses from 60 to 70 microns. The coatings were cured at 23° C. and 10° C. and 50% relative humidity (RH). The data are summarized in Table 3. The coatings containing the curing agent of the present disclosure had similar or shorter dry times than the comparative with the comparative known curing agents of aliphatic, cycloaliphatic and Mannich base at 23° C. and 10° C. The coatings using aliphatic curing agents of DETA, and TETA, and heterocyclo aliphatic amine AEP showed very poor coating appearance, and were wet, sticky and eneven.

TABLE 3

Thin film set time of the epoxy amine curing agent composition

Inventive examples

| Curing agents | | | | | | | | |
|---|---|---|---|---|---|---|---|---|
| | Ex 3 | Ex 10 | Ex 4 | Ex 5 | Ex 6 | Ex 11 | Ex 13 | Ex 14 |
| PHR | 46 | 60 | 56 | 60 | 63 | 68 | 48 | 50 |
| Thin film set time (h) (cure at 10° C.) | | | | | | | | |
| phase 1 | 3.3 | 2.5 | 1.5 | 1.8 | 1.8 | 1.7 | 4.3 | 2.3 |
| phase 2 | 6.5 | 3.5 | 4.0 | 3.0 | 3.0 | 2.6 | 8.0 | 5.9 |
| phase 3 | 17.5 | 6.6 | 9.0 | 5.0 | 4.8 | 5.0 | 9.3 | 11.1 |
| Thin film set time (h) (cure at 23° C.) | | | | | | | | |
| phase 1 | 1.2 | 1.0 | 0.9 | 0.8 | 0.8 | 0.9 | 2.0 | 1.1 |
| phase 2 | 1.9 | 1.4 | 1.4 | 1.3 | 1.3 | 1.2 | 2.6 | 1.6 |
| phase 3 | 3.9 | 2.2 | 2.2 | 1.8 | 1.8 | 1.6 | 3.5 | 2.1 |

TABLE 3-continued

Thin film set time of the epoxy amine curing agent composition

Comparative examples

| Curing agents | | | | | | | |
|---|---|---|---|---|---|---|---|
| | TETA* | DETA* | AEP* | MXDA | IPDA | A1638 | A2432 |
| PHR | 21 | 18 | 38 | 30 | 37 | 16 | 46 |
| Thin film set time (h) (cure at 10° C.) | | | | | | | |
| phase 1 | 6.5 | 10.5 | 4.3 | 5.0 | 2.5 | 5.3 | 3.2 |
| phase 2 | >24 | >24 | 8.5 | 8.0 | 11.3 | 10.4 | 4.8 |
| phase 3 | >24 | >24 | 10.8 | 9.0 | 13.8 | >24 | 8.6 |
| Thin film set time (h) (cure at 23° C.) | | | | | | | |
| phase 1 | 2.4 | 7.0 | 2.5 | 2.4 | 2.6 | 1.4 | 1.5 |
| phase 2 | >12 | >12 | 4.6 | 3.4 | 6.5 | 2.2 | 2.0 |
| phase 3 | >12 | >12 | 5.6 | 4.4 | 7.0 | 2.4 | 2.8 |

*wet, sticky, and uneven coatings

Test Example 3: The Persoz Hardness and Shore D Hardness of Epoxy-Amine Compositions The Persoz and shore D hardness test results were obtained after 1 day, 2 days, and 7 days cure at 23° C. and 10° C. and 50% RH. Persoz hardness test coatings were applied to glass panels at 75 micron WFT (wet film thickness) using a Bird applicator resulting dry film thicknesses from 60 to 70 microns, and tested in accordance with ASTM D4366. The coating specular gloss was measured at an angle of 20 degree (20°) and 60 degree (60°) using a Gardner gloss meter in accordance with ASTM D523. Measurements were made with the glass panel placed on a black cardboard background. Shore D test was performed in accordance with ASTM D2240. As shown in Table 4, the epoxy amine curing agent compositions using the curing agents of the present disclosure had fast shore D hardness development, similar to the known curing agents of aliphatic, cycloaliphatic and Mannich base at 23° C. and 10° C. The coatings using the curing agents of the present disclosure showed fast Persoz hardness development at 23° C., similar to the known curing agents of aliphatic, cycloaliphatic and Mannich base, and better gloss at 23° C. and 10° C.

TABLE 4

Persoz hardness, gloss, and shore D hardness of the epoxy amine curing agent compositions Inventive Examples

| Curing agents | Ex 4 | Ex 5 | Ex 6 | Ex 11 | Ex 13 |
|---|---|---|---|---|---|
| Shore D (23° C.) | | | | | |
| 8 Hours | 86 | 86 | 87 | 83 | 81 |
| 1 Day | 88 | 87 | 88 | 84 | 85 |
| 2 Day | 87 | 88 | 88 | 82 | 85 |
| 7 Day | 89 | 88 | 88 | 84 | 86 |
| Shore D (10° C.) | | | | | |
| 1 Day | 86 | 85 | 85 | 85 | 83 |
| 2 Day | 87 | 86 | 86 | 85 | 85 |
| 7 Day | 86 | 87 | 86 | 86 | 86 |
| Persoz (23° C.) | | | | | |
| 1 Day | 315 | 311 | 306 | 259 | 232 |
| 2 Day | 332 | 326 | 312 | 281 | 257 |
| 7 Day | 337 | 331 | 326 | 278 | 259 |
| Persoz (10° C.) | | | | | |
| 2 Day | 29 | 38 | 64 | 177 | 143 |
| 7 Day | 93 | 141 | 142 | 258 | 152 |

TABLE 4-continued

Persoz hardness, gloss, and shore D hardness
of the epoxy amine curing agent compositions Gloss

| | | | | | |
|---|---|---|---|---|---|
| 7 Day (23° C.) | 117/125 | 115/123 | 102/149 | 151/151 | 52/80 |
| 7 Day (10° C.) | 37/69 | 48/79 | 44/72 | 73/83 | 26/59 |

Comparative Examples

| Curing agents | TETA | DETA | AEP | MXDA | IPDA | A1638 | A2432 |
|---|---|---|---|---|---|---|---|
| Shore D (23° C.) | | | | | | | |
| 8 Hours | 84 | 83 | 80 | 84 | 68 | 85 | |
| 1 Day | 86 | 85 | 82 | 86 | 85 | 83 | |
| 2 Day | 86 | 86 | 82 | 86 | 86 | 86 | |
| 7 Day | 86 | 86 | 83 | 87 | 87 | 83 | |
| Shore D (10° C.) | | | | | | | |
| 1 Day | 84 | 85 | 84 | 75 | 70 | 71 | |
| 2 Day | 86 | 85 | 86 | 78 | 80 | 75 | |
| 7 Day | 86 | 85 | 85 | 76 | 82 | 81 | |
| Persoz (23° C.) | | | | | | | |
| 1 Day | nd* | nd* | 198 | 314 | 270 | 313 | 298 |
| 2 Day | nd* | nd* | 220 | 324 | 313 | 295 | 295 |
| 7 Day | nd* | nd* | 218 | 334 | 336 | 300 | 311 |
| Persoz (10° C.) | | | | | | | |
| 2 Day | nd* | nd* | nd* | 290 | 183 | 241 | 266 |
| 7 Day | nd* | nd* | nd* | 314 | 306 | 281 | 321 |
| Gloss | | | | | | | |
| 7 Day (23° C.) | 42/71 | 9/26 | 32/62 | 28/59 | 166/149 | 52/82 | 96/101 |
| 7 Day (10° C.) | nd* | nd* | nd* | 12/36 | 57/78 | 7/24 | 42/66 | nd*: wet, greasy, not determined

Test Example 4: Coating Properties of Epoxy-Amine Coating Compositions Using Diluted Epoxy Resin The coatings were prepared using a diluted epoxy resin Ancarez RZ4305 (Bisphenol-A/F resin, C12-14-glycidyl ether diluted (Epodil 748), EEW 195, viscosity 1,000 mPa·s, obtained from Air Products and Chemicals, Inc.). Table 5 summarizes the coating property. As shown in Table 5, the coatings prepared from curing agents of the present disclosure exhibited faster thin film set time, similar or better persoz hardness development and better gloss than the comparative known fast curing agent of aliphatic and Mannich base.

TABLE 5

Coating property with Ancarez RZ4305 diluted resin

| | | Inventive Examples | | Comparative examples | |
|---|---|---|---|---|---|
| | | Ex 11 in 30% benzyl | Ex 11 in 40% benzyl | | |
| | Unit | alcohol | alcohol | A1638 | A2432 |
| Thin film set time (23° C.) | | | | | |
| phase 1 | hrs | 0.9 | 0.9 | 3.1 | 1.8 |
| phase 2 | hrs | 1.4 | 1.3 | 5.2 | 2.3 |
| phase 3 | hrs | 1.7 | 1.6 | 9 | 3.1 |
| Persoz (23° C.) | | | | | |
| 4 hours | sec | 39 | 30 | 0 | 24 |
| 8 hours | sec | 94 | 41 | 13 | 76 |
| 16 hours | sec | 163 | 82 | 13 | 149 |
| 24 hours | sec | 198 | 96 | 16 | 173 |
| 48 hours | sec | 221 | 102 | 17 | 191 |
| 7 days | sec | 240 | 123 | 29 | 220 |
| Gloss (23° C.) | 20°/60° | 100/101 | 85/101 | 15/50 | 41/81 |
| Thin film set time (10° C.) | | | | | |
| phase 1 | hrs | 2.4 | 2 | 8 | 6.5 |
| phase 2 | hrs | 3.8 | 2.8 | 15 | 8 |
| phase 3 | hrs | 5.6 | 5.2 | >24 | 16 |
| Persoz (10° C.) | | | | | |
| 8 hours | sec | 15 | 15 | wet | wet |
| 16 hours | sec | 38 | 29 | wet | 15 |
| 24 hours | sec | 56 | 42 | wet | 33 |
| 48 hours | sec | 81 | 51 | wet | 38 |
| 7 days | sec | 145 | 95 | wet | 47 |
| Gloss (10° C.) | 20°/60° | 20/58 | 43/80 | 31/68 | 28/69 |

Test Example 5: Thin Film Set Time of Epoxy-Amine Coating Compositions Using the Amine Curing Agent of the Present Disclosure as Co-Curing Agent with Cycloaliphatic Curing Agent The amine curing agent of the present disclosure was used as co-curing agent with the formulated cycloaliphatic curing agent, Ancamine® 2143. This curing agent is based on a Amicure® PACM—liquid epoxy resin adduct. Amicure PACM contains; di(aminocyclohexyl)methane and includes the two main isomers 2,4-(diaminocyclohexyl)methane (5%) and 4,4'-(diaminocyclohexyl)methane (95%). Table 6 lists the formulation based on weight percentage of the components and the resultant coating properties. The results in Table 6 showed that the amine curing agent of the present disclosure could be used as an effective co-curing agent to improve the cure speed of cycloaliphatic curing agent at both ambient (23° C.) and low temperatures (10° C.).

TABLE 6

Formulation and thin film set time using co-curing agent with cycloaliphatic amine.

|  | Inventive Examples | | | Comparative Example |
| --- | --- | --- | --- | --- |
| Curing agent formulation | Ex 4 | Ex 5 | Ex 6 | A2143 |
| Neat inventive curing agent (Ex 4, 5, or 6) | 50% | 50% | 50% |  |
| Ancamine 2143 | 28% | 28% | 28% | 100% |
| PACM | 5% | 5% | 5% |  |
| Benzyl alcohol | 17% | 17% | 17% |  |
| Curing agent Viscosity (mPa · s) | 584 | 734 | 1,074 | 650 |
| Thin film set time (23° C.) | | | | |
| Phase 1 (hour) | 1.3 | 1.3 | 1.1 | 2.5 |
| Phase 2 (hour) | 2.0 | 2.0 | 1.8 | 5.3 |
| Phase 3 (hour) | 2.9 | 2.6 | 2.6 | 7.0 |
| Thin film set time (10° C.) | | | | |
| Phase 1 (hour) | 2.8 | 3.0 | 2.8 | 4.8 |
| Phase 2 (hour) | 4.8 | 5.3 | 4.3 | 12.5 |
| Phase 3 (hour) | 6.0 | 7.2 | 6.3 | 17.0 |

Test Example 6: Thin Film Set Time of Epoxy-Amine Coating Compositions Using the Curing Agent of the Present Disclosure with a Polyamide Co-Curing Agent The amine curing agent of the present disclosure was used as co-curing agent with polyamide Ancamide® 350A (A350A), a polyamide based on TOFA, dimer acid and TEPA. Table 7 lists the formulation and thin film set time in comparison with A350 accelerated by Ancamine® K54 and a commercially available phenalkamide. The results in Table 7 clearly shows that the amine curing agent of the present disclosure could be used as an effective co-curing agent to improve cure speed of polyamide at low temperature with much improve coating appearance. Comparative examples exhibit slower cure speeds and poorer coating appearance, as these still have a greasy and slightly tacky surface following 24 hrs cure at 5° C. Typically Ancamine K54 is used to accelerate polyamide. However, high level of Ancamine K54 would induce homopolymerization of epoxy and lead to poor physical property of the coating, therefore, it cannot be added at too high levels otherwise a drop off in coating performance (water resistance, corrosion resistance) may be observed. Typical use levels of K54 are <10%, preferably ≤5% based on active polyamide.

TABLE 7

Formulation and thin film set time using a polyamide co-curing agent.

| Curing agent formulation | Inventive examples Ex 11 | | Comparative Examples | |
| --- | --- | --- | --- | --- |
| Ancamide 350A | 50 | 50 | 100 | 100 |
| Neat inventive curing agent [Ex 11] | 35 | 35 |  |  |
| Benzyl alcohol | 15 |  |  |  |
| cardanol |  | 15 |  |  |
| Ancamine K54 |  |  | 4 |  |
| Phenalkamide |  |  |  | 100 |
| Thin film set time (h) (5° C.) | | | | |
| BK phase 2 | 6 | 6 | 25 | 18 | 19 |
| BK phase 3 | 16 | 12 | 48 | 30 | 30 |

In a separate formulation the new co-curing agent [Ex 5] was used in combination with a modified polyamide adduct, Ancamide 2050. This polyamide adduct is used in the coating industry for high solid protective coatings and offers moderately improved performance vs Ancamide 350A at lower application temperatures. Table 8 list compositions where A2050 has been modified with the new co-curing agent. The results in Table 8 also demonstrate that the amine curing agent of the present disclosure is an effective co-curing agent to improve both the dry speeds of the epoxy-polyamide coatings at both ambient and low temperature, while ensuring high gloss, tack free coatings after 1 day are obtained. Comparative examples exhibit slower cure speeds with the original A2050 exhibiting a tacky surface appearance after cure at 5° C. In the above formulations, the presence of Ancamine K54 offers a slight improvement with A2050, the presence of both K54 & the new co-amine curative results in significantly fast development of tack free time.

TABLE 8

Formulation and acceleration impact of new co-curing agent with high solid polyamide

| Curing agent formulation | Inventive examples Ex 11 | | | Comparative Examples | |
| --- | --- | --- | --- | --- | --- |
| Formulation | A | B | C | D | E |
| Ancamide 2050 | 85 | 80 | 80 | 100 | 97.5 |
| Neat inventive curing agent [Ex 5] | 15 | 12.5 | 10 | — | — |
| Benzyl alcohol | 7.2 | 5.8 | 4.4 | — | — |
| Ancamine K54 | 3.7 | 3.1 | 2.5 | — | 2.5 |
| Curing Agent Loading (PHR) | 65 | 65 | 65 | 70 | 65 |
| Thin film set time (h) (23° C.) | | | | | |
| BK phase 2 | 2:15 | 2:45 | 3:00 | 6:00 | 4:45 |
| BK phase 3 | 3:30 | 3:30 | 4:15 | 12:00 | 8:30 |
| Surface Appearance | Glossy Tack Free | | | | |
| Thin film set time (h) (5° C.) | | | | | |
| BK phase 2 | 8:30 | 10:00 | 11:45 | 25:30 | 17:30 |
| BK phase 3 | 15:00 | 19:30 | 24:00 | >48 | 37:00 |
| Surface Appearance 1 day | Clear glossy tack free | | | Clear-tacky | Clear slight tack |

Test Example 7: Yellowing Resistance Test

Clear coatings were applied to cold-rolled steel substrate at 150 micron wet film thickness and cured at 23° C. and 50% RH for 7 days. The coatings were then exposed to UV A light, and the delta yellowness index was measured according to ASTM E313-96 under D65 illuminant at 1 day, 3 day and 7 day UV A light exposure. Ancamine® 1856 is an MXDA Mannich base curing agent, and Ancamine® 1618 is an IPDA-adduct base curing agent and is a known yellowing resistance cycloaliphatic curing agent. The data in Table 9 shows that the coating prepared from the curing agent of the present disclosure exhibited much lower delta yellowness index than Mannich base curing agent, and better than standard cycloaliphatic curing agent.

TABLE 9

Delta yellowness index of epoxy-amine compositions

| Curing agent | | Inventive examples Ex 11 in 40% benzyl alcohol | Comparative examples | |
|---|---|---|---|---|
| | | | A1856 | A1618 |
| PHR | | 68 | 40 | 60 |
| Delta | 1 day | 5.82 | 55.08 | 2.95 |
| yellowness | 3 day | 11.38 | 60.62 | 9.47 |
| index | 7 day | 18.72 | 62.49 | 23.9 |

Test Example 8: Degree of Cure of Epoxy-Amine Compositions

Table 10 lists the degree of cure and Tg of epoxy-amine compositions. Ancamine® 1638, Ancamine® 2432, DETA, TETA and MXDA were tested for comparison. Degree of cure and Tg were determined by Dynamic Scanning calorimetry (DSC). About 5 grams of the amine-epoxy composition was mixed 3 cycles using FlackTeK DAC 250 SP SpeedMixer™ by Hauschild. Around 5-10 mg samples were placed in Tzero hermetic DSC pans and were sealed in air. The samples were analyzed using a TA Instruments Q2000 DSC calibrated in T4P mode at a heating rate of 10° C./min. with Indium. The samples were heated from −80° C. to 280° C. at 10° C./min. The samples were then cooled back to −90° C. and the test was repeated. The degree of cure was determined by subtracting the residual heat of cure after 7 days from the initial total heat of cure, then divided by the initial total heat of cure. Table 10 indicates that the curing agent of the present disclosure had high degree of cure both at 23° C. and 10° C., and Tg was similar to known fast aliphatic and Mannich base curing agent.

TABLE 10

Degree of cure and Tg of epoxy-amine compositions

| | Inventive examples | | Comparative examples | |
|---|---|---|---|---|
| | Ex 11 in 30% BzOH | Ex 11 in 40% BzOH | A1638 | A2432 |
| Degree of cure (%) (23° C. cure) | 93 | 100 | 81 | 94 |
| Tg (° C.) | 51.6 | 42.8 | 54.4 | 52.4 |
| degree of cure (%) (10° C.) | 84 | 97 | 70 | 84 |
| Tg (10° C. cure) | 33.2 | 24.1 | 35.1 | 29.4 |

Test Example 9: Chemical Resistance Test

Clear coatings were applied to cold-rolled steel substrate at 150 micron wet film thickness and cured at 23° C. and 50% RH for 7 days. A fast cure aliphatic curing agent Ancamine® 1638 was used as comparison. The coatings were then exposed to the chemicals listed in Table 11 by a patch test. A lint free cotton batch in the size of 1 inch by 1 inch was placed on the test panel. The cotton patch was at least 12 mm from the edge of the panel. The patch was dampened with the chemicals listed in Table 10, and cover with a suitable lid (e.g. heavy weight watch glass). The panels were left undisturbed for the specified time of 1 day, 2 days, 7 days, and 14 days. The cotton patch was then removed and the coatings was dried with a cloth or tissue. The coatings were examined and rated in a scale 1-5 in which 1 was the worst and 5 was the best. The data in Table 10 shows that the curing agent of the present disclosure exhibited good chemical resistance to base and organic solvents.

TABLE 11

Chemical resistance test results

| | DI Water | 50% NaOH | Ethanol | Metyl Ethyl Ketone | Xylene | Mineral Spirits |
|---|---|---|---|---|---|---|
| Ex 11 | 5 | 5 | 4 | 3 | 5 | 5 |
| A1638 | 2 | 1 | 1 | 1 | 3 | 4 |

Rating of 1-5

| 1 | 2 | 3 | 4 | 5 |
|---|---|---|---|---|
| Coating degraded/ destroyed | Tiny blisters/ loss gloss | Reduced/ loss gloss | Softened, edge mark | no change |

Test Example 10: Mechanical Properties of the Epoxy-Amine Composition

Table 12 lists the formulation of epoxy-amine composition with diluted resin. Tensile strength test was performed in accordance with ASTM D638 type I. The results show that the epoxy-amine composition exhibited fast cure at low temperature of 10° C. and good shore D hardness development. At the meantime, the composition showed high flexibility, with strain at break of 30-40% and high modulus. This tough and flexible composition particular useful in applications where strength and flexibility are required such as overlay coating for concrete bridge deck and road pavement.

TABLE 12

Property of epoxy-amine composition

| Curing agent formulation | Curing agent 1 | Curing agent 2 |
|---|---|---|
| Neat inventive curing agent [Ex 11] | 10.03 | 10.03 |
| Benzyl alcohol | | 2.61 |
| Cardanol | 10.03 | 7.42 |
| Resin: 90% Epon 828/10% Epodil 748 (EEW 195) | 23.1 | 23.1 |
| Stoichiometry (amine/epoxy) | 1.1 | 1.1 |
| Curing agent viscosity (mPa · s) | 2,470 | 1,241 |
| Mix Viscosity (mPa · s): | 1,767 | 1,367 |
| Time to 12,000 mPa · s (min): | 26.5 | 30.5 |
| Thin film set time at 10° C./50% RH | | |
| phase 1 (hours) | 2.0 | 2.2 |
| phase 2 (hours) | 3.0 | 3.1 |
| phase 3 (hours) | 3.7 | 4.7 |
| Shore D (5 days at 23° C./50% RH) | 75 | 70 |

TABLE 12-continued

| Property of epoxy-amine composition | | |
|---|---|---|
| Curing agent formulation | Curing agent 1 | Curing agent 2 |
| Tensile strength test (7 day 23° C./50% RH) | | |
| Load at Max. Load (lbf) | 328.1 | 197.5 |
| Stress at Max. Load (psi) | 2,530 | 1,476 |
| Stress at Break (psi) | 2,529 | 1,473 |
| % Strain at Break (%) | 32.6 | 45.9 |
| Modulus (Automatic Young's) (psi) | 110,463 | 14,827 |

Test Example 11: Coating Properties of Pigmented Formulation

Thin film set time of epoxy-amine coating compositions using the curing agent of the present disclosure with a Mannich co-curing agent Table 13 lists the formulations of pigmented coatings using the curing agent of the present disclosure, in comparison with known fast curing agents Ancamine® 2609W, and Sunmide CX-1151. Ancamine® 2609W is an MXDA Mannich base, and Sunmide CX-1151 an MXDA phenalkamine. The coatings for cross hatch adhesion and blush resistance were applied on cold-rolled steel substrate. The adhesion test was performed on coatings after cure for 7 days at designated temperatures. Blush resistance was performed by adding a drop of 1% aqueous solution of phenapthalene to the coating after 1 day and 2 day cure. The results in Table 14 clearly show that the amine curing agent of the present disclosure is a low yellowness index and fast curing agent at low temperature, with cure speed similar to known fast cure Mannich base and phenalkamine.

TABLE 13

| | Pigmented coating formulations | | | |
|---|---|---|---|---|
| | Inventive examples | | | |
| | Formulation 1 including Ex 11 | | Formulation 2 including Ex 11 | |
| Formulations | Weight | Volume | Weight | Volume |
| PART A | | | | |
| Epon 828 | 54.48 | 5.62 | 54.48 | 5.62 |
| Nuosperse 657 | 1.8 | 0.23 | 1.8 | 0.23 |

TABLE 13-continued

| | Pigmented coating formulations | | | |
|---|---|---|---|---|
| Epodil LV-5 | 7.12 | 0.85 | 7.12 | 0.85 |
| BYK D410 | 0.5 | 0.05 | 0.5 | 0.05 |
| Talc | 18.7 | 0.82 | 18.7 | 0.82 |
| TiO$^2$ | 17.4 | 0.52 | 17.4 | 0.52 |
| Total Part A | 100 | 8.09 | 100 | 8.09 |
| Part B | | | | |
| Xylene | 17.43 | 2 | 17.43 | 2 |
| Benzyl alcohol | 0 | 0 | 0 | 0 |
| Bentone SD | 1.57 | 0.13 | 1.57 | 0.13 |
| Nuosperse 657 | 1.5 | 0.19 | 1.5 | 0.19 |
| cimbhar BF | 22.85 | 0.56 | 22.85 | 0.56 |
| Talc | 20.15 | 0.87 | 20.15 | 0.87 |
| Ex 11 in 40% benzyl alchol | 36.5 | 4.35 | | |
| Ex 11 in 40% cardanol | | | 36.5 | 4.35 |
| Sunmide CX-1151 | | | | |
| Ancamine 2609W | | | | |
| Total Part B | 100 | 8.1 | 100 | 8.1 |

| | Comparative examples | | | |
|---|---|---|---|---|
| | CX1151 | | A2609W | |
| | Weight | Volume | Weight | Volume |
| PART A | | | | |
| Epon 828 | 54.48 | 5.62 | 54.48 | 5.62 |
| Nuosperse 657 | 1.8 | 0.23 | 1.8 | 0.23 |
| Epodil LV-5 | 7.12 | 0.85 | 7.12 | 0.85 |
| BYK D410 | 0.5 | 0.05 | 0.5 | 0.05 |
| Talc | 18.7 | 0.82 | 18.7 | 0.82 |
| TiO$_2$ | 17.4 | 0.52 | 17.4 | 0.52 |
| Total Part A | 100 | 8.09 | 100 | 8.09 |
| Part B | | | | |
| Xylene | 0 | 0 | 17.43 | 2 |
| Benzyl alcohol | 0 | 0 | 15 | 1.73 |
| Bentone SD | 1.57 | 0.13 | 1.57 | 0.13 |
| Nuosperse 657 | 1.5 | 0.19 | 1.5 | 0.19 |
| cimbhar BF | 22.85 | 0.56 | 22.85 | 0.56 |
| Talc | 20.15 | 0.87 | 20.15 | 0.87 |
| Ex 11 in 40% benzyl alcohol | | | | |
| Ex 11 in 40% cardanol | | | | |
| Sunmide CX-1151 | 70 | 8.24 | | |
| Ancamine 2609W | | | 21.6 | 2.56 |
| Total Part B | 116.07 | 9.99 | 100.1 | 8.04 |

TABLE 14

| Property of the pigmented coating formulations | | | | |
|---|---|---|---|---|
| | Inventive examples | | | |
| | Coating 1 (based on formulation 1/ Table 13) | | Coating 2 (based on formulation 2/ Table 13) | |
| Thin film set time (h) | 25° C. | 2° C. | 25° C. | 2° C. |
| Phase 1 | 2.5 | 5.0 | 2.5 | 5.0 |
| Phase 2 | 4.0 | 6.0 | 4.0 | 6.0 |
| Phase 3 | 6.0 | 8.0 | 6.0 | 8.0 |
| Specular Gloss (60°) | 50 | | 45 | |
| X- Hatch adhesion (7 day cure) | Pass | | Pass | |
| Blush Resistance (Phenapthalene Indicator test) | Slight/Slight | | None/None | |
| Persoz Hardness (1 day) 25° C. | 127 | | 127 | |

TABLE 14-continued

| Property of the pigmented coating formulations | | |
|---|---|---|
| Persoz Hardness (1 day) 2° C. | 58 | 40 |
| Yellowness Index | 2.02 | 2.05 |

| | Comparative examples | |
|---|---|---|
| | CX1151 | A2609W |
| Thin film set time (h) | 25° C.   2° C. | 25° C.   2° C. |
| Phase 1 | 4.0       5.0 | 2.0       4.0 |
| Phase 2 | 5.0       6.0 | 4.0       6.5 |
| Phase 3 | 6.5       8.0 | 5.0       7.0 |
| Specular Gloss (60°) | 60 | 52 |
| X-Hatch adhesion (7 day cure) | Pass | Pass |
| Blush Resistance (Phenapthalene Indicator test) | Slight/Slight | None/None |
| Persoz Hardness (1 day) 25° C. | 129 | 128 |
| Persoz Hardness (1 day) 2° C. | 29 | 32 |
| Yellowness Index | 5.9 | 1.65 |

Test Example 12: Ultra Low Temperature Cure Properties of a Coating Composition Using Co-Curing Agent The clear epoxy-amine coating compositions using the present disclosure as a co-curing agent with phenalkamine Sunmide CX-1151 were listed in Table 15. Fast curing agent Sunmide CX-1151 was blended with the curing agent of the present disclosure at a 50/50 wt ratio and tested for thermal properties and MEK double rub. The MEK double rub test is an indicator of how well the through cure properties of the film have developed. The higher the number of MEK double rubs, then the grater the film integrity. Fast Mannich base curing agents Ancamine® 2609W, and Ancamine® 1856 were also blended with Sunmide CX-1151 at 50/50 wt ratio and tested for comparison. The coatings were applied on cold-rolled steel substrate for MEK double rubs test, and on glass for thin film set time at 75 micron wet film thickness. The coatings were then cured at −6° C. The MEK double rubs test was performed after cure at −6° C. for 7 days. The data in Table 15 shows that the curing agent of the present disclosure as co-curing agent improved the MEK double rubs significantly over Mannich base curing agent at −6° C., with high degree of cure and Tg.

TABLE 15

| | Coating properties using co-curing agent | | | |
|---|---|---|---|---|
| | Inventive example | Comparative examples | | |
| Curing agent | EX-11 (50%) CX-1151 (50%) | A2609W (50%) CX-1151 (50%) | A1856 (50%) CX-1151 (50%) | CX-1151 |
| PHR | 62 | 61 | 60 | 134 |
| Thin film set time (h) (cure −6° C.) | | | | |
| Phase 2 | 9 | 9 | 7 | 7.5 |
| Phase 3 | 14 | 12 | 9 | 13.5 |
| MEK Double Rubs | | | | |
| −6° C. | 200 | 38 | 42 | 113 |
| 25° C. | 200 | 190 | 200 | 200 |
| % Cure by DSC | | | | |
| −6° C. | 79% | 84% | 78% | 56% |
| 25° C. | 83% | 87% | 90% | 98% |

TABLE 15-continued

| | Coating properties using co-curing agent | | | |
|---|---|---|---|---|
| | Inventive example | Comparative examples | | |
| Curing agent | EX-11 (50%) CX-1151 (50%) | A2609W (50%) CX-1151 (50%) | A1856 (50%) CX-1151 (50%) | CX-1151 |
| Tg (cure −6° C./7 day) | | | | |
| 1st scan | 34 | 40 | 48 | 16 |
| 2nd scan | 64 | 64 | 51 | 64 |

Test Example 13: Coating Composition Using Co-Curing Agent

Figure 2:
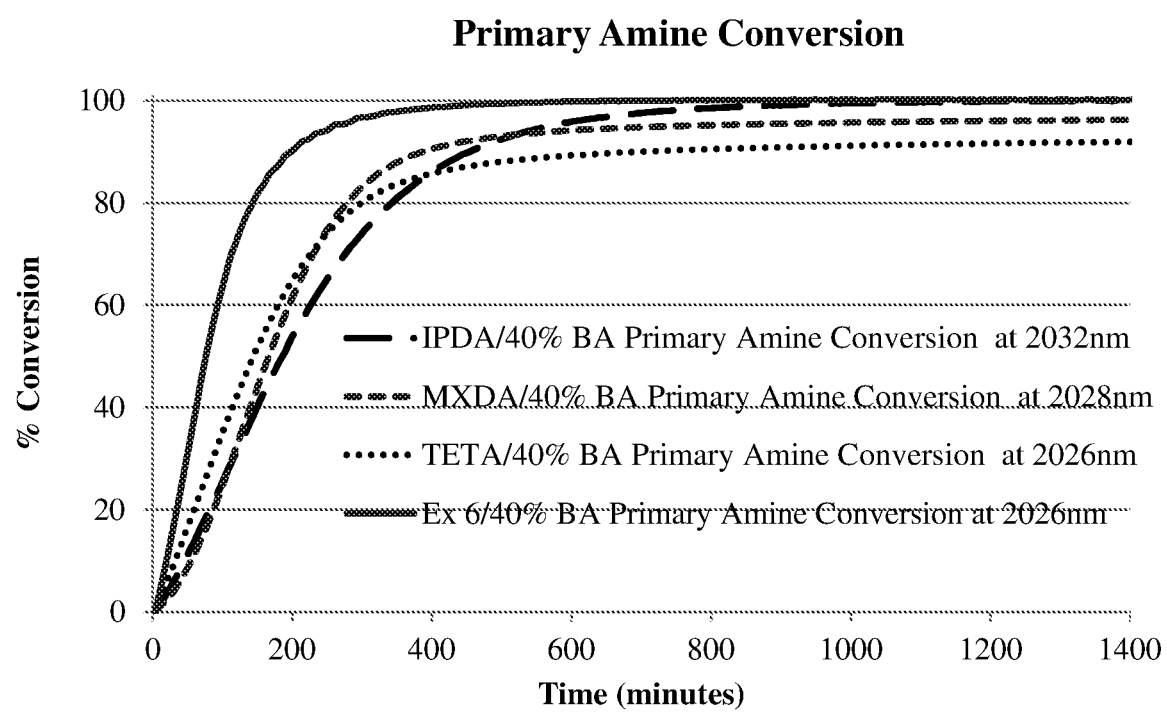
FIG. 2 a graphical representation showing primary amine conversion determined by near infrared spectroscopy according to exemplary embodiments of the invention and comparative amine-epoxy curing agents.

The amine-epoxy composition using curing agent of Example 6 in 40% benzyl alcohol (BA) with Epon 828 was analyzed. TETA, MXDA and IPDA were analyzed as comparison. The semi-quantitative analysis of amine-epoxy composition was carried out by near infrared spectroscopy (NIR). The conversion of oxirane (epoxy) and primary amine during the cure was monitored by the C—H stretch of oxiran ring at 1646 cm-1, and the N—H stretch of the primary amine at 2026 cm-1, respectively. About 5 grams of the amine-epoxy composition was mixed using FlackTeK DAC 250 SP SpeedMixer™ by Hauschild. After mixing, the sample was placed in a disposable sample cell of 0.8 mm path length, and placed in a 25° C. oven. The NIR spectrometer used for the analysis was a Model 6500 near-infrared spectrometer equipped with an Interactance probe by Foss NIR Systems, Inc. The IR spectra were collected over about 24 hours, and the spectra were analyzed using GRAMS software. FIG. 1 shows the conversion of epoxy and FIG. 2 the primary amine conversion in amine-epoxy composition using the curing agent of the present disclosure. TETA, MXDA and IPDA were analyzed as comparison. FIGS. 1 and 2 clearly indicated that amine-epoxy composition using the curing agent of the present disclosure had higher degree of conversion of epoxy group and primary amine group than the known aliphatic, and cycloaliphatic curing agents.

Test Example 14: Curing Agent Formulations for Resin Transfer Moulding

Several amine curing agent formulations using curing agent of Example 5 were formulated to evaluate their potential for use in a resin transfer moulding process. Curing agent mixtures were prepared by combining and mixing the components given in examples. They were then thoroughly mixed stoichiometrically and thoroughly (amine/epoxy ratio was 1:1) with the epoxy component of standard bisphenol-A based epoxy resin of Epon 828, EEW 190, unless specified otherwise. Amines were obtained from Air Products and Chemicals, Inc. Table 16 the properties of the inventive examples are shown in comparison with comparative curing agents. The results pointed out that the inventive examples have similar or improved properties over the comparative examples, while the inventive examples do not make use of DETA, which comes with poor health and safety features.

TABLE 16

Curing agent compositions for resin transfer moulding and their properties

| Formulations | Inventive examples | | | Comparative example | |
|---|---|---|---|---|---|
| Amicure PACM | 50 | 62 | 70 | 50 | 62 |
| Diethylenetriamine (DETA) | | | | 40 | 10 |
| Neat inventive curing agent [Ex 5] | 40 | 10 | 20 | | |
| 3-aminopropylcyclohexyl amine | | 18 | | | 18 |
| Tertiary amine accelerator | 10 | 10 | 10 | 10 | 10 |
| Properties | | | | | |
| TPeak DCS 1$^{st}$ run | 110 | 113 | 112 | 104 | 110 |
| Mix viscosity @ 120° C. (mPa · s) | 30 | 50 | 25 | 20 | 20 |
| Time to 200 mPa · s @ 120° C. (s) | 40 | 52 | 54 | <20 | 68 |
| Time to gel point @ 120° C. (min) | 2.1 | 3.2 | 2.5 | 1.4 | 2.7 |
| Tg DSC rerun (° C.) | 86 | 100 | 100 | 112 | 100 |

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. An amine-epoxy curing agent comprising the contact product of:
   (a) an amine epoxy curing agent having at least one saturated heterocyclic compound having two nitrogen heteroatoms according to formula (I):

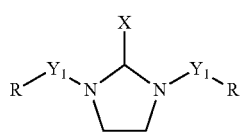

(I)

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups; and
   (b) at least one multifunctional amine having three or more active amine hydrogens per molecule.

2. The amine-epoxy curing agent of claim 1, wherein the at least one multifunctional amine is selected from the group consisting of an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a glycidyl ether of bisphenol A or bisphenol F or an epoxy novolac resin, and combinations thereof.

3. A method for forming an epoxy comprising reacting an amine epoxy curing agent with at least one multifunctional epoxy resin, where:
   the amine-epoxy curing agent comprises at least one saturated heterocyclic compound having two nitrogen heteroatoms according to formula (I)

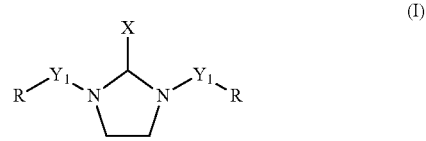

(I)

where X is independently selected from a hydrogen atom, a linear or branched $C_1$ to $C_4$ alkyl groups and a substituted or un-substituted phenyl group, $Y_1$ is a direct bond or a divalent polyethylene polyamine group having 1 to 8 nitrogen atoms and R is independently a hydrogen atom or a group selected from $C_1$-$C_8$ linear, cyclic, and branched alkyl, alkenyl, and alkaryl groups.

4. The amine-epoxy curing agent of claim 1, wherein X and R are H.

5. An amine-epoxy composition comprising an amine-epoxy curing agent and at least one multifunctional epoxy resin, wherein the amine-epoxy curing agent comprises at least one saturated heterocyclic compound having two nitrogen heteroatoms according to formula (I):

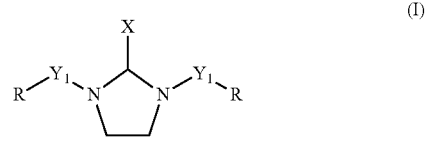

(I)

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups, and further comprises at least one multifunctional amine having three or more active amine hydrogens per molecule.

6. The amine-epoxy composition of claim 5, wherein X and R are H.

7. The amine-epoxy composition of claim 5, wherein the at least one multifunctional amine is selected from the group consisting of an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a glycidyl ether of bisphenol A or bisphenol F or an epoxy novolac resin, and combinations thereof.

8. A cured epoxy resin obtained from the composition of claim 5.

* * * * *